US010654608B2

(12) United States Patent
Lizari Illarramendi et al.

(10) Patent No.: US 10,654,608 B2
(45) Date of Patent: May 19, 2020

(54) LABELLING DEVICE FOR SYRINGES FOR PHARMACEUTICAL PRODUCTS

(71) Applicant: Kiro Grifols, S.L., Arrasate (ES)

(72) Inventors: Borja Lizari Illarramendi, Vitoria-Gasteiz (ES); Susana Soto Iglesias, Arrasate-Mondragon (ES); Asier Lizarriturri Martiarena, Aretxabaleta (ES); Amaia Ilzarbe Andres, Donostia-San Sebastian (ES)

(73) Assignee: Kiro Grifols, S.L., Arrasate (Gipuzkoa) (ES)

( * ) Notice: Subject to any disclaimer, the term of this patent is extended or adjusted under 35 U.S.C. 154(b) by 43 days.

(21) Appl. No.: 16/105,250

(22) Filed: Aug. 20, 2018

(65) Prior Publication Data
US 2019/0100343 A1 Apr. 4, 2019

(30) Foreign Application Priority Data

Oct. 4, 2017 (EP) .................................. 17382663

(51) Int. Cl.
*B65C 9/40* (2006.01)
*B65C 9/04* (2006.01)
*B65C 3/16* (2006.01)
*B65C 9/06* (2006.01)
*B65B 3/00* (2006.01)
(Continued)

(52) U.S. Cl.
CPC ..................................... *B65C 9/40* (2013.01);
*A61J 1/00* (2013.01); *A61M 5/178* (2013.01);
*B65B 3/006* (2013.01); *B65B 57/02* (2013.01);
*B65B 61/26* (2013.01); *B65C 3/14* (2013.01);
*B65C 3/16* (2013.01); *B65C 9/04* (2013.01);
*B65C 9/067* (2013.01); *B65C 9/36* (2013.01);
*B65C 2009/0003* (2013.01)

(58) Field of Classification Search
CPC .... B65C 3/14; B65C 3/16; B65C 9/04; B65C 9/065; B65C 9/067; B65C 9/36; B65C 9/40; B65C 2009/0003; B65B 3/006; B65B 57/02; B65B 61/26; A61J 1/00; A61M 5/178
See application file for complete search history.

(56) References Cited

U.S. PATENT DOCUMENTS 3,835,987 A 9/1974 Gess
5,771,657 A * 6/1998 Lasher .................... B65B 61/20
53/55
2008/0195077 A1 8/2008 Anatrini

FOREIGN PATENT DOCUMENTS

EP 2500288 A2 9/2012

OTHER PUBLICATIONS

Extended European Search Report for Application No. 17382663.7, dated Mar. 27, 2018 in 10 pages.

* cited by examiner

*Primary Examiner* — George R Koch
(74) *Attorney, Agent, or Firm* — Knobbe, Martens, Olson & Bear, LLP

(57) ABSTRACT

A labelling device for syringes for pharmaceutical products includes a carousel that holds and transports syringes, a syringe labelling station, a syringe handler, a camera for detecting the position of the marker scale of the syringes. The syringe labelling station includes an arm responsible for holding the label by a suction system and two articulated gates arranged such that when the syringe passes therethrough, the gates apply pressure over the body of the syringe in such a way that the label is affixed uniformly over the body.

16 Claims, 25 Drawing Sheets

(51) Int. Cl.
*A61M 5/178* (2006.01)
*A61J 1/00* (2006.01)
*B65C 9/36* (2006.01)
*B65B 57/02* (2006.01)
*B65C 3/14* (2006.01)
*B65B 61/26* (2006.01)
*B65C 9/00* (2006.01)

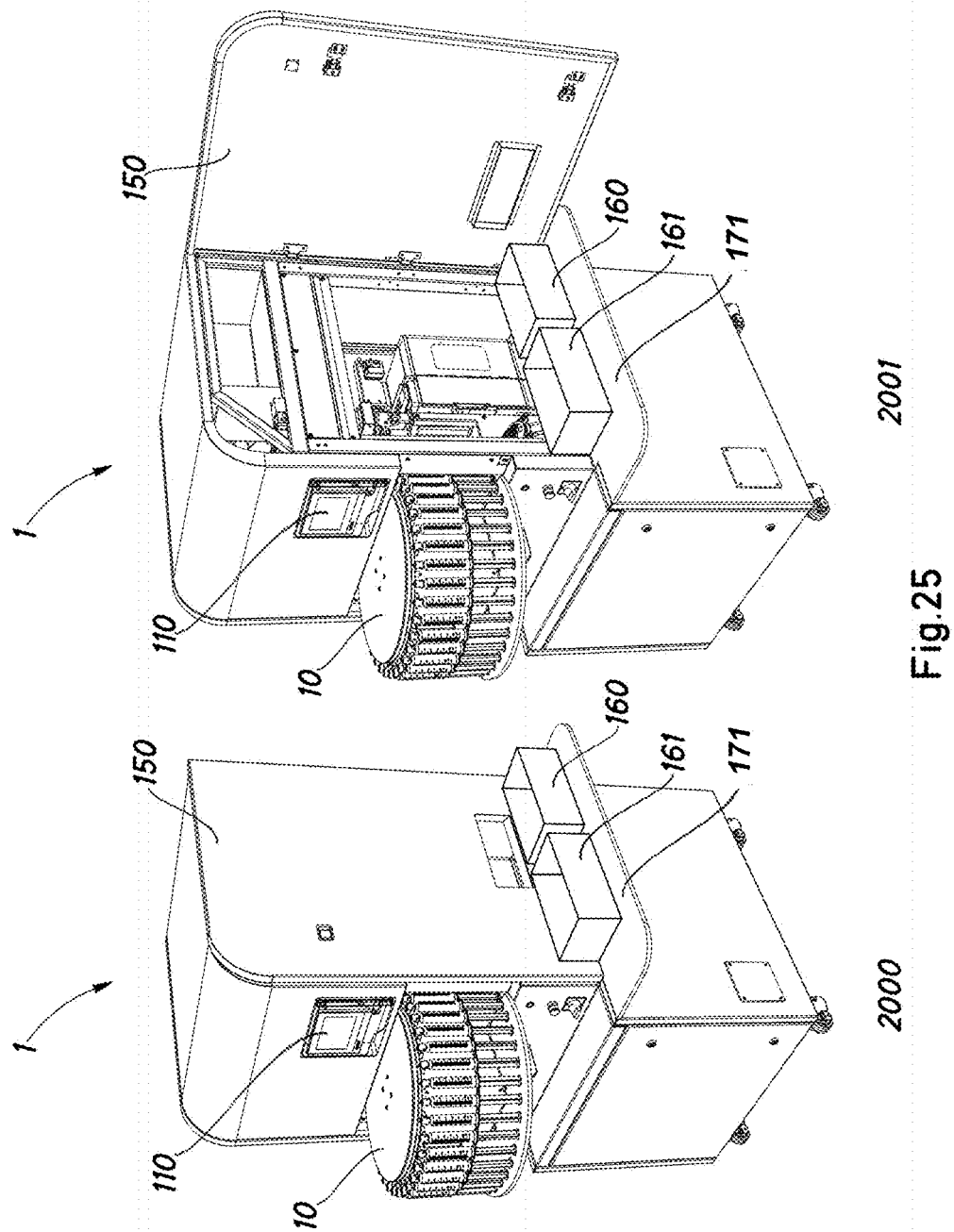

LABELLING DEVICE FOR SYRINGES FOR PHARMACEUTICAL PRODUCTS

FIELD OF THE INVENTION

The present invention relates to an automatic syringe labeller for any type of drug. Preferably, said drugs are oncological drugs. Preferably, said oncological drugs are in a liquid state.

BACKGROUND OF THE INVENTION

The use of oncological drugs for the treatment of cancer is known. Notable among the various types of oncological drugs are antineoplastic drugs.

Within the group of antineoplastic drugs, cytostatic drugs stand out. Cytostatics are cytotoxic substances designed for and used in, preferably, chemotherapy. To improve the therapeutic effect thereof and reduce the side effects caused in the patient, at present this type of medicine is prepared individually and tailored to each patient, which leads to in situ handling, in hospitals, for example, of this type of drug.

Owing to the action mechanism thereof at cellular level, cytostatics may have mutagenic, carcinogenic or teratogenic effects, and therefore the handling of this type of product is governed by numerous regulations to minimise the exposure of medical and/or pharmaceutical staff to this type of product. Accordingly, at present preparation of medicine to be administered to the patient is usually carried out in semi-automated or fully automated stations.

The medicine to be administered to the patient is usually packaged in syringes. To ensure the traceability of said syringes in order to ensure that the correct medicine is administered to the patient and in the correct dose, it is important to correctly label the syringe which contains the drug to be administered.

Various types of syringe labellers are known in the prior art.

Patent document PCT WO 2010/105334 A1 discloses an automatic system for preparing medicines in bags, which act as a source for preparing doses of highly diluted medicine in syringes. As well as means for preparing and measuring the doses of the medicines to be administered to patients, said device also comprises robotic means for handling syringes and a label printing and application station responsible for printing labels and applying said labels to the syringes. Said labels may contain a bar code or any other computer-readable code, which in turn contains information about the patient, the type of drug in the syringe, etc.

Said label printing and application station comprises a printing system and a printing platen. After positioning and fixing the label on the platen, the robotic syringe handling means arrange a syringe on the platen in such a way that the axis of the syringe is perpendicular to the longitudinal axis of the label and in the midpoint thereof. The syringe rests, in a first contact, on the surface of the label in order to affix said label to the syringe. Said first contact occurs in a deflection zone of the platen which can be driven down by pressure. Thus, the robotic syringe handling means push the syringe downwards in said deflection zone of the platen, allowing the label to adhere around said syringe.

The automatic medicine preparation system disclosed in document WO 2010/15334 A1 has the drawback, among others, that the medicine handling and preparation station is combined with the syringe labelling station in the same device. Owing to the exacting sterility requirements for the preparation of medicines, the presence of the labelling system could be a source of contamination of said medicine.

US patent document US 2008/0195077 A1 discloses a syringe labelling system which comprises a rotating plate which in turn comprises a plurality of external cavities, uniformly distributed about the axis of said rotating plate, each cavity being designed to transport a syringe on a circular trajectory. Said circular trajectory extends between a loading station, in which the syringes are inserted in the respective cavities, and an unloading station, in which each syringe, after being checked, is removed from the relevant cavity and directed to a rejection or acceptance path.

Situated between the loading and unloading stations is a marking station, in which each syringe receives a label, said marking station comprises a device for unwinding a continuous strip which holds the labels, a device for recovering the strip once said strip has passed through the marking station with no labels thereon, and a plate, around which the strip is wound, said plate being bent into an L shape, so that the labels can be unstuck one after the other.

The marking station comprised in the syringe labelling system disclosed by document US 2008/0195077 A1 comprises the supply of a rolling channel designed to wrap the body of each syringe in the corresponding label, causing the syringe to rotate on its own longitudinal axis after a longitudinal axis of the label has been placed in contact with the body of the syringe by a line which converges in the marking station and which is designed to provide an ordered succession of labels.

One of the drawbacks of the labelling system disclosed by document US 2008/0195077 A1 is that said system does not have means to prevent the marker scale of the syringe from being covered by the label. Accordingly, the labels used in said labelling system have a transparent border to allow the marker scale of the syringe to be seen, and although this may be a valid solution in some cases, it is not an optimal solution.

SUMMARY OF THE INVENTION

The present invention overcomes the above-mentioned problems by disclosing a labelling device for syringes for pharmaceutical products which comprises a carousel having means for holding and transporting syringes, a syringe labelling station, a syringe handling device, means for detecting the position of the marker scale of the syringes and in which the syringe labelling station comprises an arm responsible for holding the label by means of a suction system and two articulated gates arranged such that when the handling means cause the syringe to pass therethrough, said gates apply pressure over the body of the syringe in such a way that the label is affixed uniformly over said body.

In addition to the above-mentioned problems, one of the most important problems when labelling syringes is to ensure the traceability of said syringe in order to ensure that the label corresponds exactly to the medicine contained therein. Said problem is also overcome, according to another aspect of the present invention. To do this, the syringe labelling device also comprises at least one RFID reader, a control device and a label printer, and the control device is configured to transmit the data read by the at least one RFID reader to the label printer.

An advantage of the present invention consists in separating the preparation of the medicine and the respective packaging thereof from the labelling phase, which allows the syringe labelling device to be positioned outside the clean room where this type of medicine must be prepared.

Being able to position the syringe labelling device outside the clean room allows the size of said clean room to be reduced, or leaves room for new instruments, and reduces the risk of contamination.

Cytostatic medicines are usually prepared in automatic or semi-automatic devices and are usually packaged in syringes for the administration of said medicines to patients. In medicine preparation devices, an RFID label is placed on each syringe for the identification thereof. Said RFID label may contain, among other details, information about the composition of the medicine, about the patient to whom the medicine is to be administered, expiry date, etc. At present, there are at least two main types of RFID labels for syringes: disposable labels and reusable labels. Various embodiments of the syringe labelling device of the present invention exist which are capable of working with syringes having disposable RFID labels and various embodiments capable of working with syringes having reusable RFID labels. Preferably, the syringes are hermetically sealed by a stopper placed in the coupling cone thereof.

Embodiments of the labelling device exist which also allow batches of preparations to be left in quarantine, which batches are traced using the corresponding RFID label, until, once the batch has been released after ascertaining the results of sterility tests, etc., said batch can be labelled.

According to an aspect of the present invention, the labelling device labels syringes which contain medicines requiring high traceability. In an embodiment, the labelling device labels syringes which contain non-toxic medicines which must be administered intravenously. In another embodiment, the labelling device labels syringes which contain cytostatic medicines or other medicines that are toxic and/or hazardous to health.

In an embodiment of the present invention, the syringe labelling device comprises a carousel having means for holding and transporting syringes. In said carousel, the user is responsible for loading the syringes having the corresponding RFID label that have come from the automatic or semi-automatic medicine preparation device. Preferably, said means for holding the syringes hold said syringes by the stopper. Still more preferably, said means for holding the syringes are produced by 3D printing. In an embodiment, the means for holding the syringes comprise two deformable tabs which hold the syringe by dimensional interference. Said two tabs are diametrically opposite with respect to the stopper of the syringe. In another embodiment, the means for holding the syringes comprise three deformable tabs which hold the syringe by dimensional interference. Of said three tabs, two are diametrically opposite with respect to the stopper of the syringe and the other holds the stopper of said syringe from above.

In a preferred embodiment, the user may load a plurality of syringes on the carousel when the labeller is stopped. A still more preferred embodiment allows the user to keep loading syringes on the carousel while the labeller is in operation.

In an embodiment, the carousel is actuated by a stepper motor. Advantageously, said carousel has at least one axial bearing. Still more advantageously, said axial bearing is a cylindrical roller bearing.

Preferably, the carousel rotates in a clockwise direction.

In an embodiment, the labelling device comprises a syringe handler. In an advantageous embodiment, said syringe handler is a robotic arm. Preferably, said syringe handler may be moved along the axes X and Y. Still more preferably, said syringe handler may be moved along the axes X, Y and Z.

In an embodiment, the syringe handler comprises a clamp suitable for holding syringes. In a preferred embodiment, said clamp is capable of rotating about its own longitudinal axis. Advantageously, said clamp comprises two claws. Still more advantageously, the claws of the clamp are shaped so as to allow the syringe to be held by at least three points, that is, the clamp holds the syringe by at least three points. Preferably, the clamp holds the syringe by the stopper thereof. By holding the syringe by the stopper, which is usually a standard component of any type of syringe, syringes of any size can be handled, with little or no modification of the holding clamp. Preferably, the claws of the clamp have pneumatic actuation means.

In an embodiment, the labelling device comprises means for detecting the position of the marker scale of the syringes. Preferably, the means for detecting the position of the marker scale of the syringes comprise a video camera. Still more preferably, said video camera is housed in a support that can be adjusted in rotation and in height. Advantageously, said video camera is controlled by specialised software.

Said means for detecting the position of the marker scale of the syringes are used to avoid concealing the marker scale of the syringes with the label. Said means for detecting the position of the marker scale of the syringes act in a coordinated manner with the syringe handler. The control device is responsible for coordinating said syringe handler with said means for detecting the position of the marker scale of the syringes. When the syringe handler is holding a syringe, said handler keeps turning said syringe until the means for detecting the marker scale detect that the syringe is in the correct position to prevent, in the next phase of labelling, the label from concealing the marker scale of the syringe totally or in part. It is very important that the medical staff who will subsequently administer the medicine to the patient can read the marker scale of said syringe at all times.

In an embodiment, the labelling device for syringes for pharmaceutical products comprises a syringe labelling station. Said syringe labelling station comprises an applicator element responsible for holding the label by suction and for placing the label on the syringe. Preferably, the applicator element is planar. Still more preferably, the design of said applicator element is such as to allow the use of labels of different types and of different sizes. Preferably, the applicator element has a sensor which detects when the label positioned on said applicator element makes contact with the syringe. Advantageously, the applicator element is connected to a retractable arm by a plurality of resilient means. Preferably, said resilient means connect the applicator element to a plate which is rigidly connected to the retractable arm. Advantageously, said retractable arm has pneumatic actuation means. Preferably, the retractable arm has two operating positions, a first for picking up the label and a second for affixing the label to the syringe. In embodiments in which the labelling station has a label printer, preferably, the label pick-up position of the retractable arm coincides with the label dispenser of said printer.

Preferably, the applicator element places the label on the syringe in such a way that the axis of the syringe is perpendicular to the longitudinal axis and at the midpoint thereof, although other arrangements are also possible.

In an embodiment, the labelling station also comprises means for detecting the correct positioning of the labels on the syringes. In an embodiment, the labelling station also comprises means for detecting the correct printing of the labels of the syringes. Preferably, said means for detecting the correct printing of the labels comprise a bar code reader and/or Data Matrix reader, preferably comprised in the printer, and responsible, at the same time as the label is being printed, for checking that the printing of said label is correct. In an embodiment, the labelling station comprises a support for badly labelled syringes and a substitute support where the faulty labels are affixed. If the printer detects that the label has been wrongly printed, the syringe handler leaves the syringe that was supposed to be labelled on a support and takes a substitute support to which the incorrect or badly printed label is affixed. The printer then reprints a label for the syringe waiting on the support and, if the printing is correct, the handling device removes the syringe from the waiting support and resumes the labelling process.

In an embodiment, the labelling station allows labelling using at least flag, half-flag and wraparound labels. Preferably, the labelling station uses labels having a paper support. However, other embodiments in which the labels do not have a paper support are also possible.

In an embodiment, the syringe labelling station comprises a label printer. Unlike numerous solutions of the prior art, the printer according to the present invention prints the labels one by one in a manner customised to each syringe. Preferably, the label printer comprises a paper support re-winder which separates the label from the paper support thereof, so that when the applicator element is holding the label by suction, said label is ready to be affixed to the syringe.

In an embodiment, the labelling station comprises two articulated gates arranged in such a way that when the handling means cause the syringe to pass therethrough, said gates apply a uniform pressure over the body of the syringe so that the label is affixed uniformly over said body. Preferably, each of the articulated gates comprises at least one hinge having at least one resilient torsion means.

Alternatively, the articulated gates comprised in the labelling station are replaced by at least two parallel rollers arranged on supports designed to accommodate the variability in size of the syringes that pass therebetween and to apply a uniform pressure over the body of the syringe so that the label is affixed uniformly over the body of the syringe.

In an embodiment, the labeller comprises at least one RFID reader. Said RFID reader reads the RFID labels of each of the syringes and allows the control device, by comparing the readings obtained with a database, to ascertain what product is contained in each of the syringes and what should be printed on the label.

In an embodiment, the syringe labelling device also comprises a precision scale. Preferably, the control device compares the reading of said precision scale with the reading of the at least one RFID reader. Still more preferably, said high precision scale is housed above at least one silent block. Said at least one silent block is used to dampen vibrations that may interfere with the reading of the high precision scale.

The weighing of the syringe is used to detect possible dosage errors in the preparation of the medicine to be administered to the patient. The data obtained when weighing the syringe are compared with the theoretical data of the contents obtained from a database. The data obtained from weighing the syringe are transferred to the database and, optionally, are subsequently printed on the label identifying each syringe.

The weighing of the syringe, together with the identification of each syringe by the corresponding RFID label thereof and the comparison of the data with the database, allows possible errors in the preparation of the medicine to be detected. If the data obtained from weighing the syringe do not coincide with those of the preparation phase of the medicine, said syringe will subsequently be labelled as a rejected preparation or not suitable for therapeutic use.

In an embodiment, the labelling device for syringes for pharmaceutical products comprises at least one receptacle for syringes that are suitable for therapeutic use and at least one receptacle for syringes that are not suitable for therapeutic use. Once the syringe has been correctly identified and labelled, the syringe handler allows said syringes to fall into a chute which takes said syringe to the corresponding receptacle. If the syringe is correctly labelled and is suitable for therapeutic use, said syringe falls into the at least one receptacle for syringes that are suitable for therapeutic use, and if the syringe is not properly labelled or has been catalogued as a rejected preparation, said syringe falls into the at least one receptacle for syringes that are not suitable for therapeutic use. Once this step of the labelling process is complete, the suitable syringes are ready to be administered to the relevant patient and the unsuitable syringes must be suitably destroyed or reviewed by specialist staff.

In an embodiment, the labeller comprises a roller of which the shaft is mounted in a cam and is arranged in such a way that said roller vertically repositions syringes that are badly positioned on the carousel.

In an embodiment, the labeller comprises an arm which laterally repositions syringes that are badly positioned on the carousel.

In an embodiment, the labelling device is suitable for labelling syringes that comprise a disposable RFID label. Preferably, said disposable RFID labels are incorporated in the stopper of the syringes.

In an embodiment, the labelling device is suitable for labelling syringes that comprise a reusable RFID label. Preferably, said reusable RFID labels are incorporated in a stopper known as a label holder which may be attached to the stopper of the syringes. As well as being able to be attached to the stopper of the syringes, the reusable RFID labels may also be separated from said syringe stopper.

In an embodiment, the labelling device comprises a mechanism for removing reusable RFID labels which in turn comprises a reusable RFID label reader and said reusable RFID label removal mechanism is actuated by the syringe handler, that is, the reusable RFID label removal mechanism does not have a motor or similar which actuates said mechanism. In an advantageous embodiment, the reusable RFID label removal mechanism also comprises a mechanism having three binary links, each of the nodes of said binary links being housed in the corresponding groove along which said nodes slide when said mechanism is actuated, one of said binary links being actuated by the syringe handler. In a still more advantageous embodiment, the reusable RFID label removal mechanism comprises means for holding the stopper of the syringe during the removal of the reusable RFID label.

In an embodiment, the upper circular plate of the carousel having means for holding and transporting syringes comprises a hole for each of the syringes said carousel can hold, said hole being suitable for the passage therethrough of the reusable RFID stopper of the corresponding syringe. In an advantageous embodiment, the labelling device comprises a basket for collecting the reusable RFID labels that have been removed.

Preferably, the corresponding reusable RFID label is removed from the syringe before the handling of said syringe, that is, before the syringe handler is holding said syringe.

The geometry of said RFID label removal mechanism is such that when the syringe handler approaches the carousel to take a syringe and carry said syringe to the weighing station, or directly to the labelling station depending on whether or not the embodiment actually has a weighing station, contact is made with one of the links of the mechanism and this in turn actuates the remaining components so as to remove the label holder from the corresponding syringe. During the removal process, the RFID reader incorporated in the removal mechanism reads the RFID label and identifies the syringe. Once the label holder has been removed, said label holder falls through a hole of the carousel and is taken to a collection basket which can be accessed from the front portion of the machine. Every so often, the user collects the used label holders and takes said holders to the medicine preparation station to be erased, placed on a new syringe and rewritten with the information for the new syringe on which said holders are placed.

Preferably, the labeller also comprises a manually actuated RFID reader. Preferably, the labeller comprises a bar code reader.

In an embodiment, the labeller is operated automatically. In an embodiment, the labeller is operated manually. In an advantageous embodiment, the labeller allows manual and automatic operation.

In manual operation, the user opens at least one of the panels which enclose the labelling device. Preferably, the at least one panel which is opened in manual operation is the side panel closest to the labelling station. Thus, the user has access to the manual RFID reader, to the bar code reader and to the printer.

In manual operation, the user reads the RFID label of the syringe using the manually actuated reader which the labeller may comprise and then manually affixes the label printed by the printer to the syringe. The bar code reader which can also be accessed by opening the side panel closest to the labelling station is used to read the codes of the labels when said labels are loaded in the printer, in order to check that said label is the type that corresponds to the preparation to be labelled (size, colour, etc.).

In an embodiment, the labeller has a plurality of wheels. Preferably, said plurality of wheels has a brake. Said plurality of wheels allows the labeller to be moved easily.

The concept of a labelling device and of a labeller is used in an equivalent and interchangeable manner throughout the present document. Throughout the text, the terms labelling device for syringes for pharmaceutical products and syringe labelling device are used in an equivalent and interchangeable manner. In this document, the directions horizontal, vertical, up, down, etc. should be understood in relation to the normal work position of the labelling device, that is, with the axial axis of said labelling device being perpendicular to the floor.

BRIEF DESCRIPTION OF THE DRAWINGS

To aid understanding, the accompanying drawings are given as an explanatory but non-limiting example of an embodiment of the labelling device for syringes for pharmaceutical products according to the present invention.

FIG. 25 shows in perspective the first embodiment of a syringe labelling device according to the present invention prepared for automatic operation and prepared for manual operation.

In the figures, similar or equivalent elements have been identified with identical reference numerals.

DETAILED DESCRIPTION OF THE PREFERRED EMBODIMENTS

Figure 1:
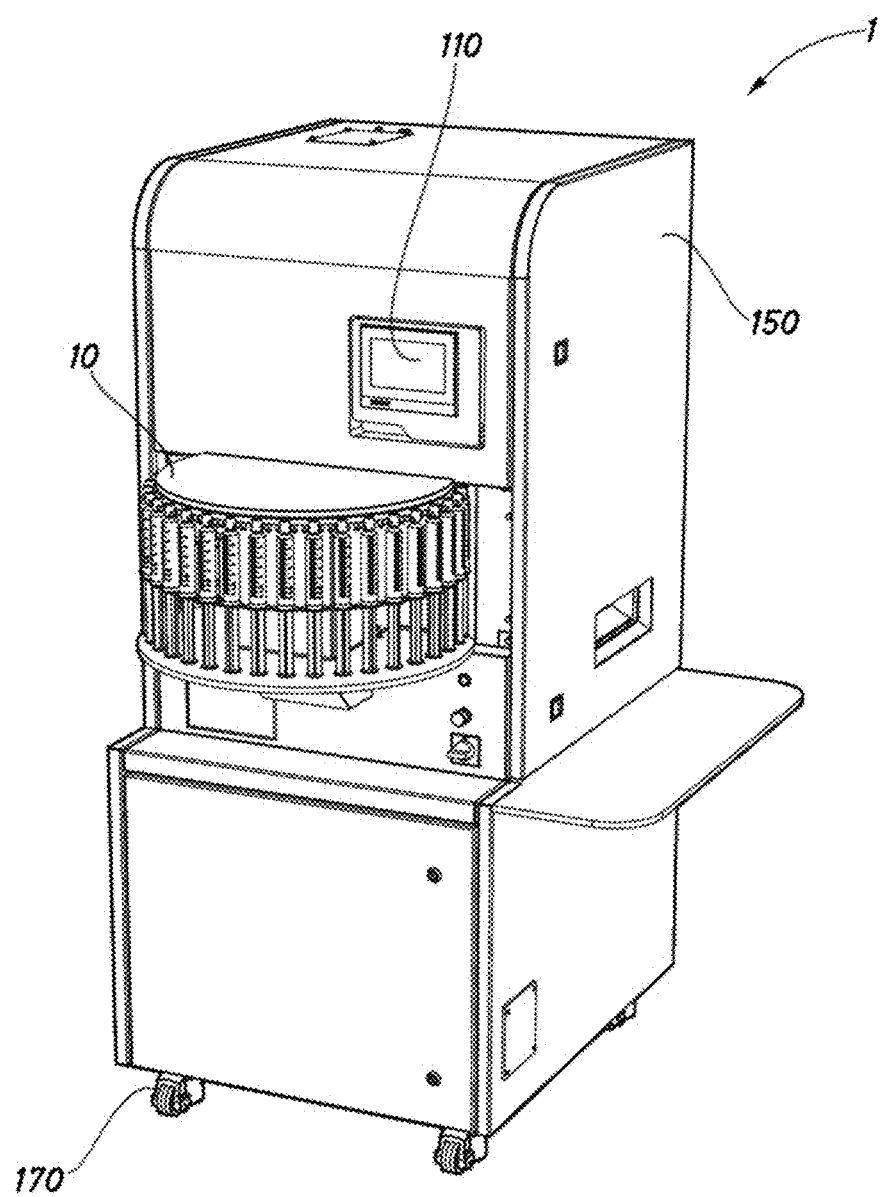
FIG. 1 is a perspective view of a first embodiment of a syringe labelling device according to the present invention.

FIG. 1 shows a first embodiment of a syringe labelling device according to the present invention. As can be seen, the labeller -1- comprises a carousel -10- having means for holding and transporting the syringes and a screen -110-, in this case a touch screen, for inputting commands, receiving alerts, etc. In addition, the labelling device -1- has a side door -150- which is opened to allow access to the interior of the labelling device -1-. As will be explained below, the opening of said side door -150- is particularly important when the labeller -1- is operating manually. In addition to the above, the labeller -1- has a plurality of wheels -170- having brakes which allow said labeller -1- to be moved easily.

Figure 2:
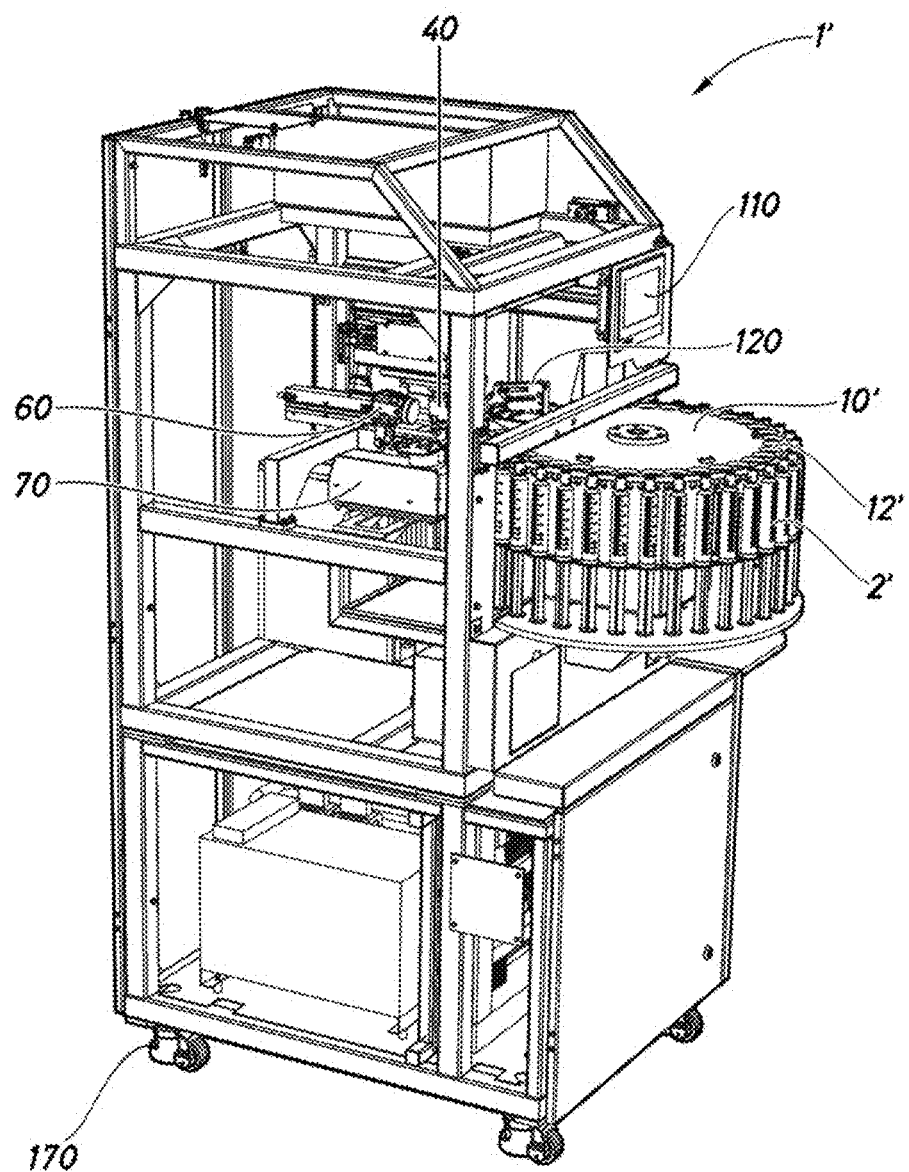
FIG. 2 is a perspective view of a second embodiment of a syringe labelling device according to the present invention with some of the outer panels removed.

FIG. 2 shows a second embodiment in perspective of a syringe labelling device according to the present invention. In order to improve the visibility of the internal components, in FIG. 2 the labeller -1'- has been shown without some of the outer panels. This makes it possible to see that, as well as the carousel -10'- having means for holding syringes -2'- having reusable RFID labels, this embodiment has, among others, a precision scale -70-, a video camera -60-, a reusable RFID label removal mechanism -120-, a robotic arm -40-, a screen -110- and a plurality of wheels -170-.

In the first and in the second embodiments shown in the various figures, the precision scale -70- corresponds to the weighing station, the video camera -60- corresponds to the means for detecting the marker scale of the syringes and the robotic arm -40- acts as a syringe handler.

Because in FIG. 2 the vast majority of the outer panels have not been shown, it can be seen that in the second embodiment, the upper circular plate of the carousel -10'- has a plurality of holes -12'- intended to allow the passage of the reusable RFID labels -202- (see FIG. 22) after being removed by the mechanism -120-.

Figure 3:
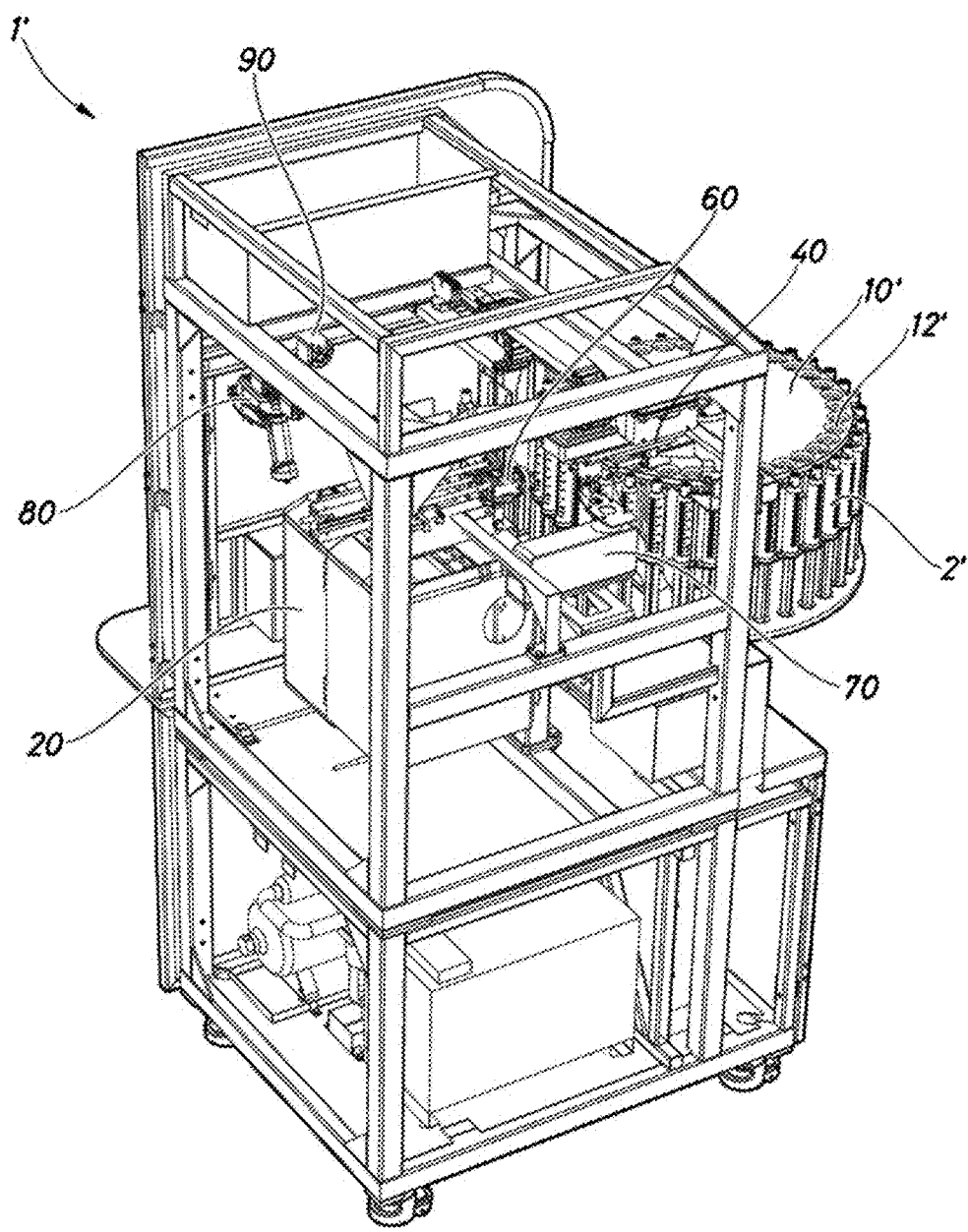
FIG. 3 is a perspective view of the second embodiment of a syringe labelling device according to the present invention with some of the outer panels removed.

FIG. 3 shows the embodiment of FIG. 2 but from a different perspective, allowing elements to be seen which in the previous figure were concealed. Thus, in addition to the majority of the above-mentioned components, the label printer -20-, the manually operated bar code reader -80- and the RFID reader -90-, also manually operated, can be seen.

Figure 4:
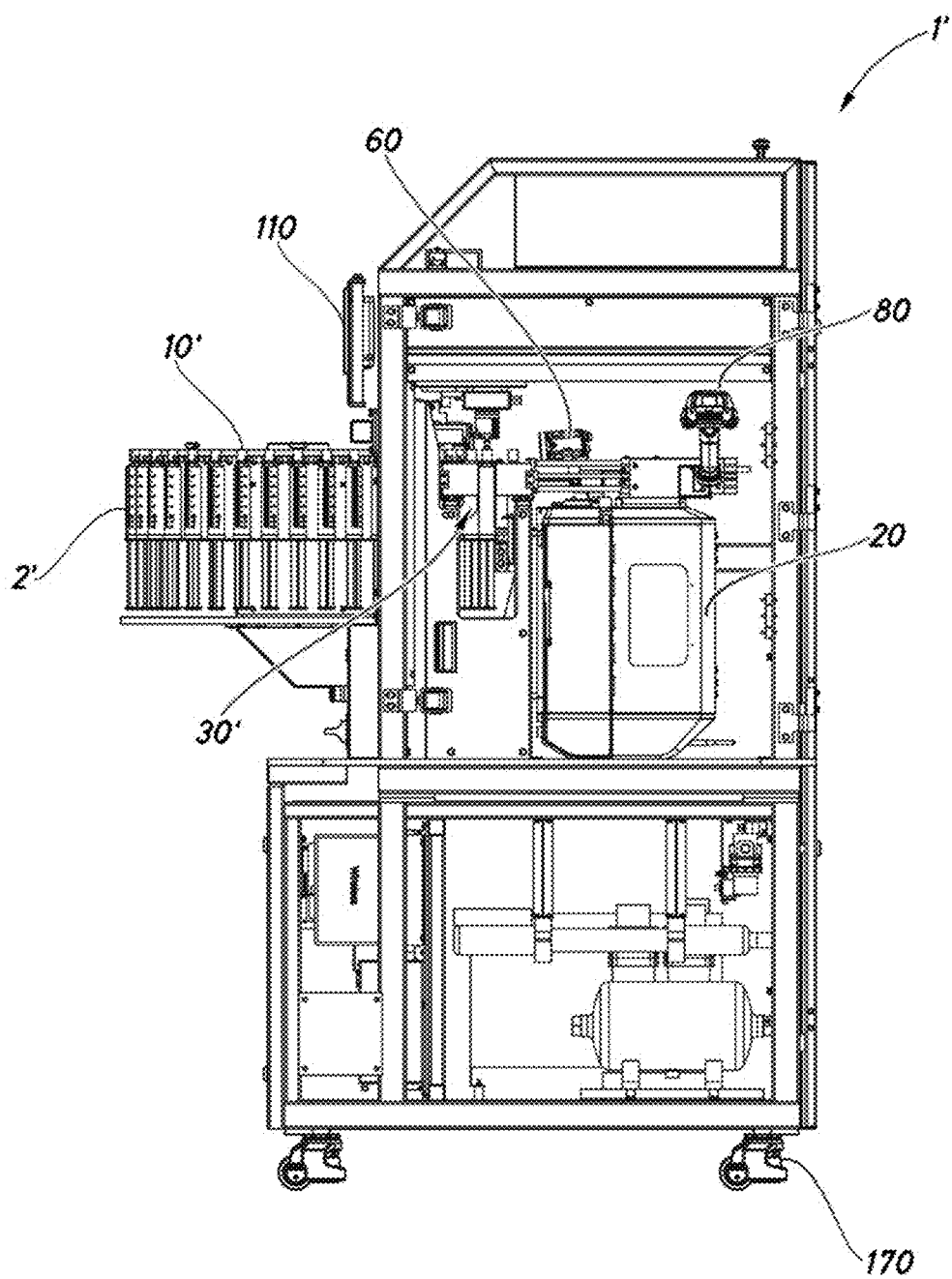
FIG. 4 is a view in side elevation of the second embodiment of a syringe labelling device according to the present invention with some of the outer panels removed.
Figure 5:
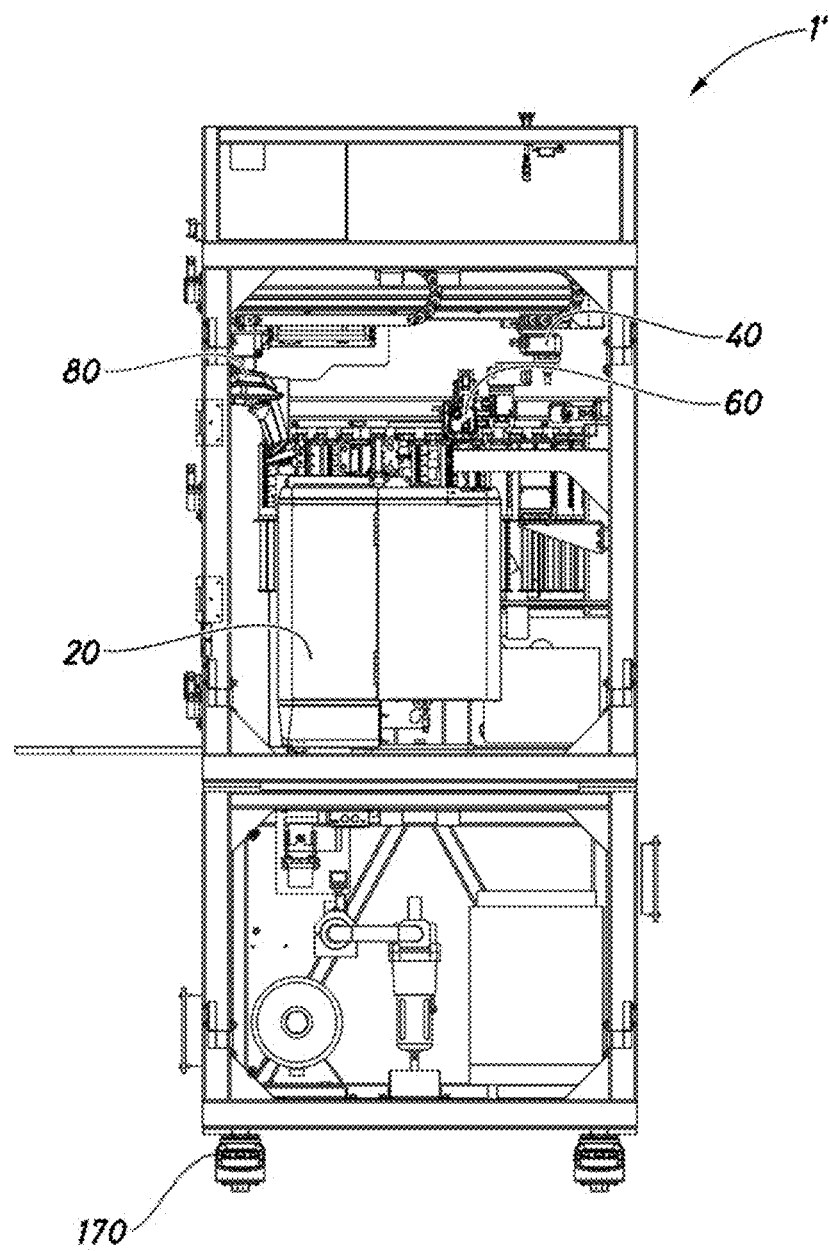
FIG. 5 is a view in rear elevation of the second embodiment of a syringe labelling device according to the present invention with some of the outer panels removed.

FIGS. 4 and 5 are views in side and rear elevation, respectively, of the second embodiment of a labeller according to the present invention. Both figures show that the main elements for labelling the syringes are positioned in the central zone of the labelling device -1'-, whereas the vast majority of the auxiliary elements such as pumps, power supply, control elements, etc. are positioned in the lower portion of the labelling device -1'-. Accordingly, in both figures, the doors and outer panels have not been shown. As well as the components already mentioned, FIG. 4 allows the labelling station -30'- of the second embodiment to be seen. Said labelling station -30'- will be described in detail later.

Figure 6:
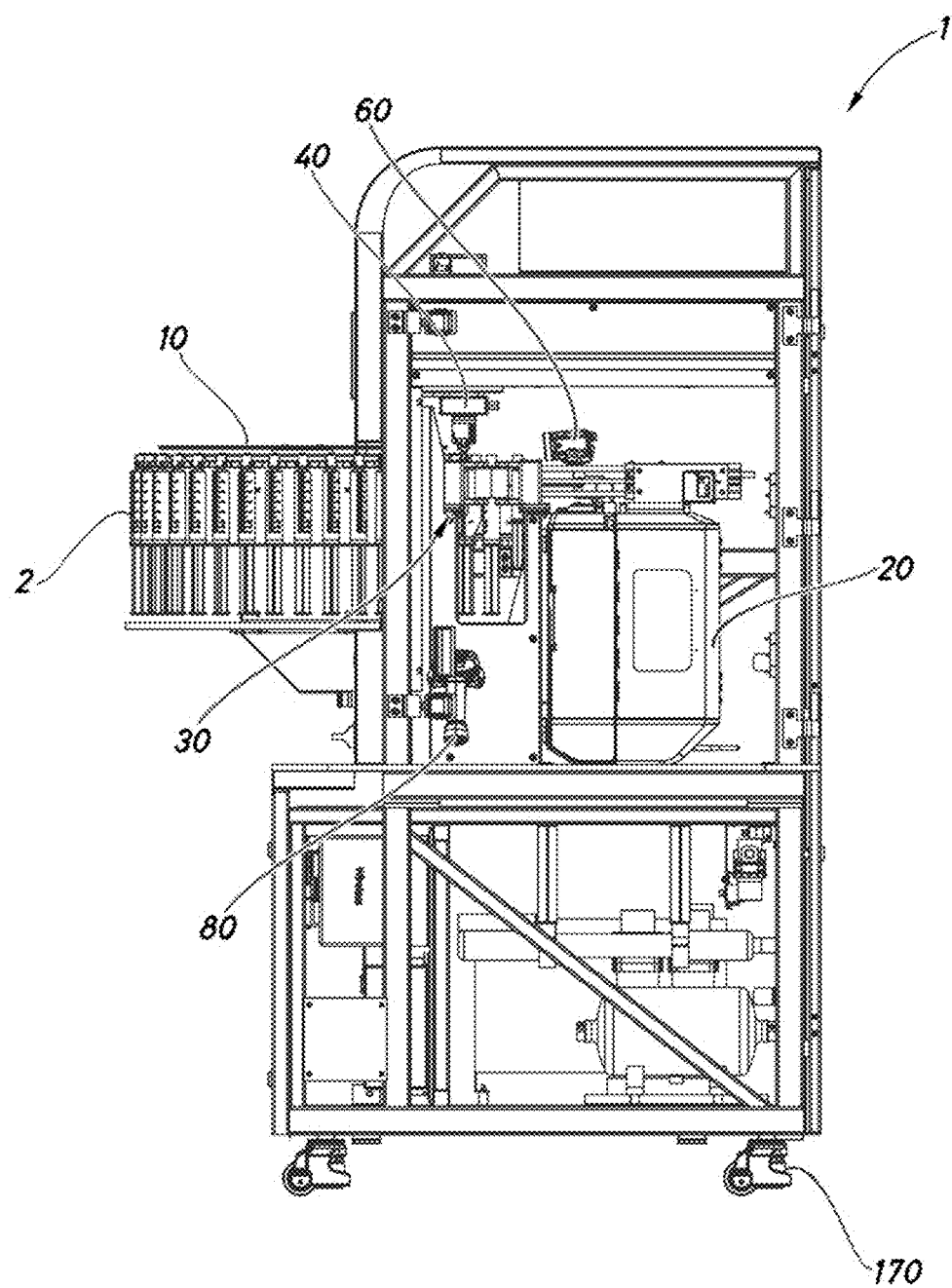
FIG. 6 is a view in side elevation of the first embodiment of a syringe labelling device according to the present invention with some of the outer panels removed.
Figure 7:
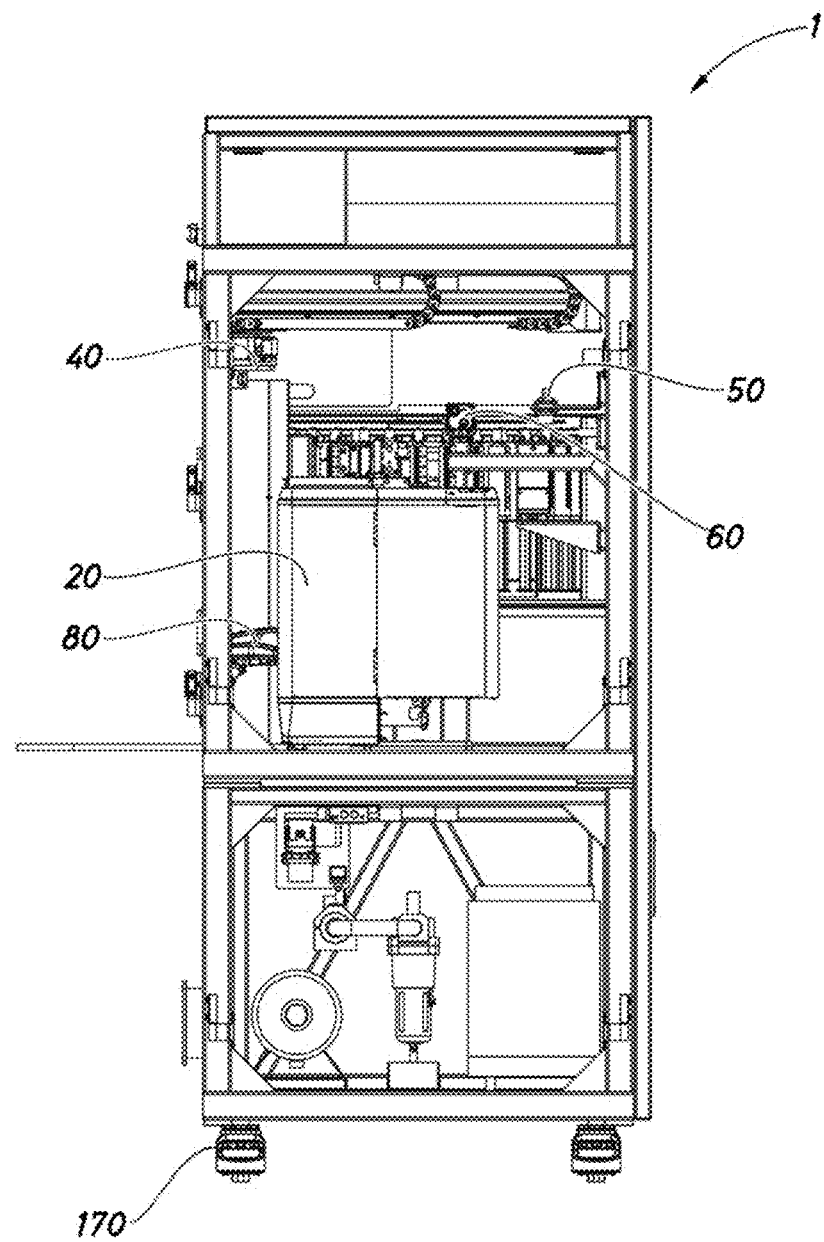
FIG. 7 is a view in rear elevation of the first embodiment of the syringe labelling device according to the present invention with some of the outer panels removed.

FIGS. 6 and 7 are views in side and rear elevation, respectively, of the first embodiment of a labeller according to the present invention. As in FIGS. 4 and 5, and in order to make it easier to see the internal components, in these figures the outer panels, doors, etc. have not been drawn. FIG. 6 shows that the labelling station -30- of the first embodiment is different from that of the second embodiment (see FIG. 4). The differences between the two will be detailed below. One of the differences between the two embodiments is that the first embodiment has an independent RFID reader -50-, whereas in the second embodiment said RFID reader is incorporated in the reusable RFID label removal mechanism -120-.

The main difference between the two embodiments shown in the figures is that in the first embodiment syringes are labelled which comprise a disposable RFID label, whereas in the second embodiment syringes are labelled which comprise a reusable RFID label. Each embodiment has a distinct labelling station -30-, -30'-, but embodiments of syringe labellers which comprise a disposable RFID label with the labelling station -30'-, and vice versa, are also possible.

Figure 8:
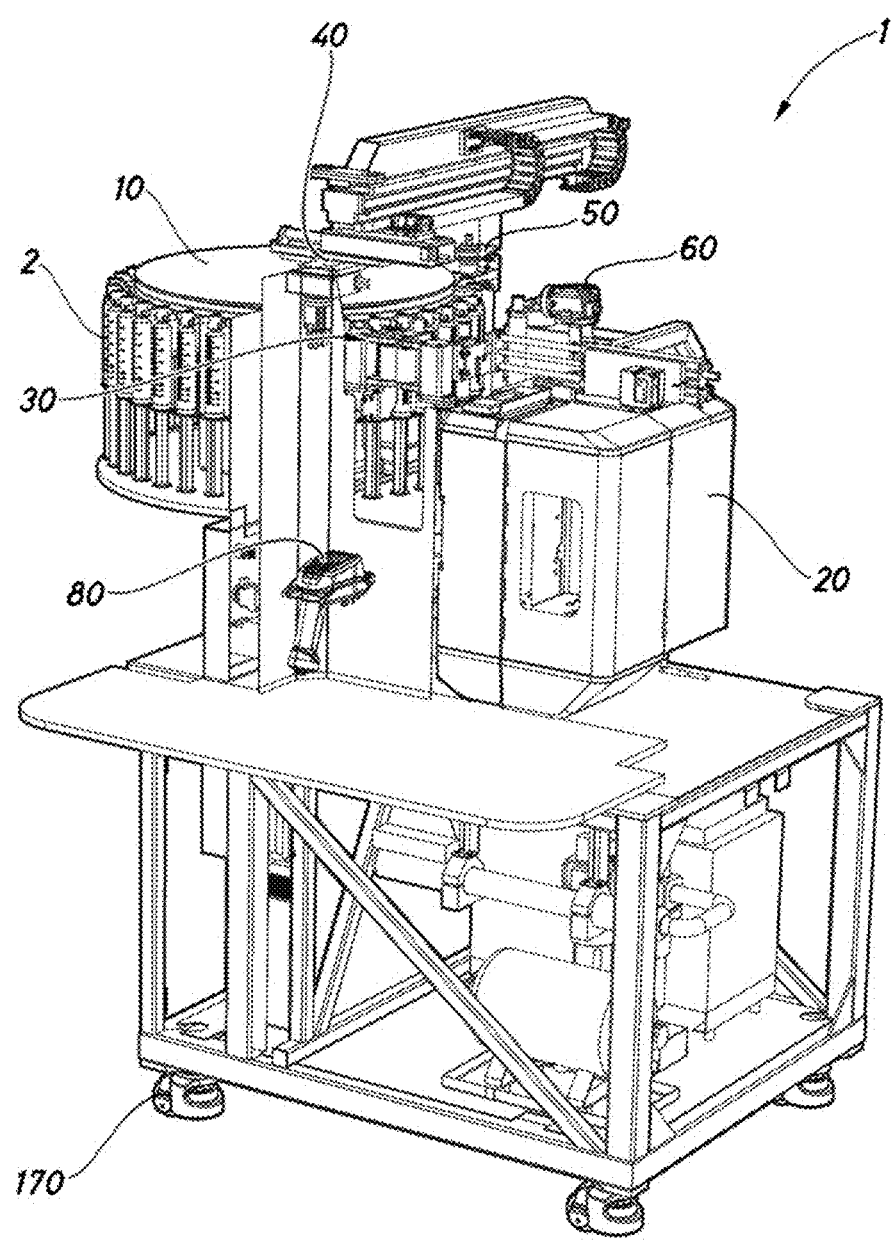
FIG. 8 is a perspective view of the first embodiment of a syringe labelling device according to the present invention without the outer panels and with the support structure removed.

FIG. 8 shows the first embodiment of a syringe labelling device according to the present invention in perspective without the outer panels and with the support structure removed. The main components of the labelling device -1- can therefore be seen clearly, as can the auxiliary components of the robotic arm -40-.

Figure 9:
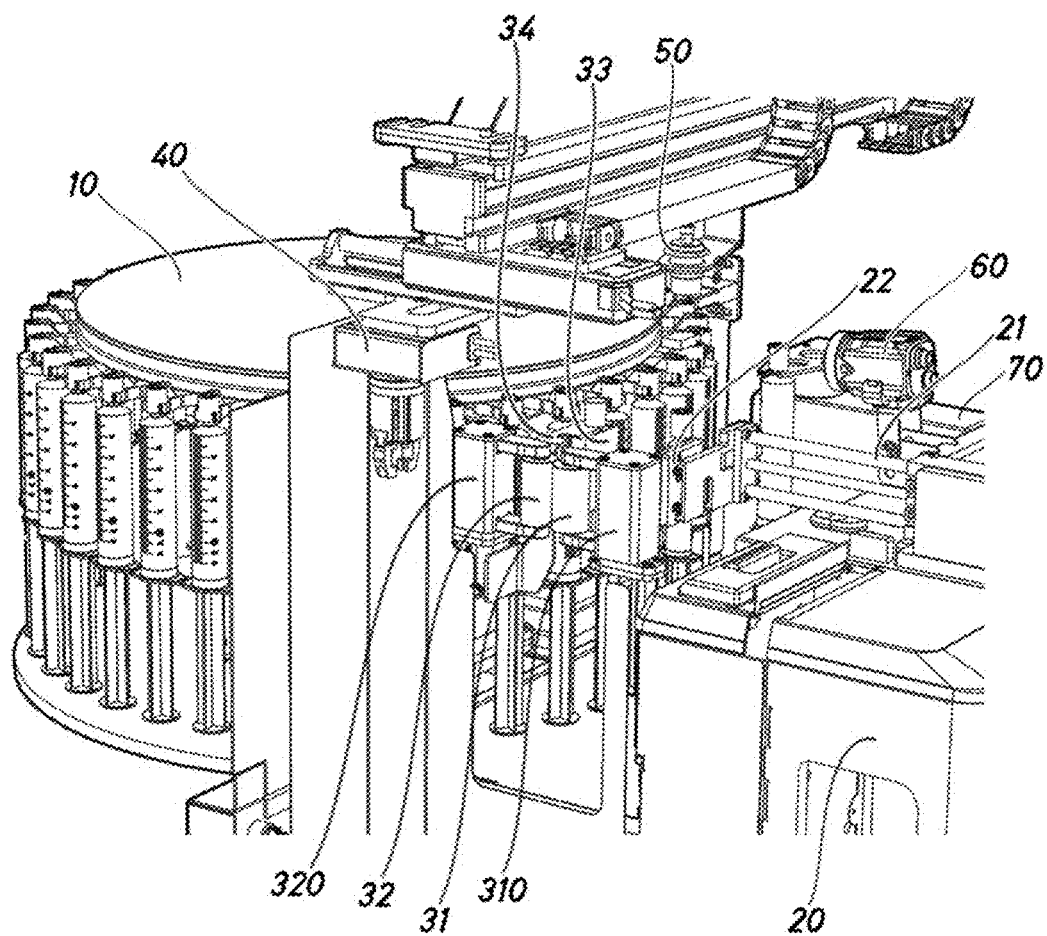
FIG. 9 is a perspective view of the labelling station of the first embodiment of a syringe labelling device according to the present invention without the outer panels and with the support structure removed.

FIG. 9 shows the labelling station of the first embodiment of a syringe labelling device according to the present invention in perspective. In the same way as in the previous figure, in this figure neither the structural elements nor the outer panels have been shown, which could make it difficult to see the key elements of the labelling station. This figure makes it possible to see in detail that, as well as the printer -20-, the labelling station comprises two parallel rollers -31-, -32- arranged on supports -310-, -320-, and that said supports and the corresponding rollers are opposite each other. Each of the supports -310-, -320- has springs designed to absorb the movement caused by the passage of syringes of different sizes between the rollers -31-, -32-.

This figure also shows that the labelling station also comprises a support -34- for syringes and a substitute support -33- to which labels that are badly printed, faulty, etc. are affixed. It also shows that the printer -20- has a retractable arm -21- and an element -22- for applying the printed labels to the syringes. Said retractable arm -21- has pneumatic actuation means and has two operating positions, a first position for picking up the printed label and a second position for affixing the label to the syringe. The applicator element -22- is connected by a plurality of springs to a plate which is rigidly connected to the end of the retractable arm -21-. The applicator element is responsible for holding the printed label until the retractable arm is extended and the label makes contact with the syringe, at which moment the applicator element -22- stops holding the label. The applicator element -22- holds the label by suction, and owing to the plurality of springs to which said applicator element is connected, said applicator element is able to absorb the small impacts against the syringe in order to deposit the label thereon.

Figure 10:
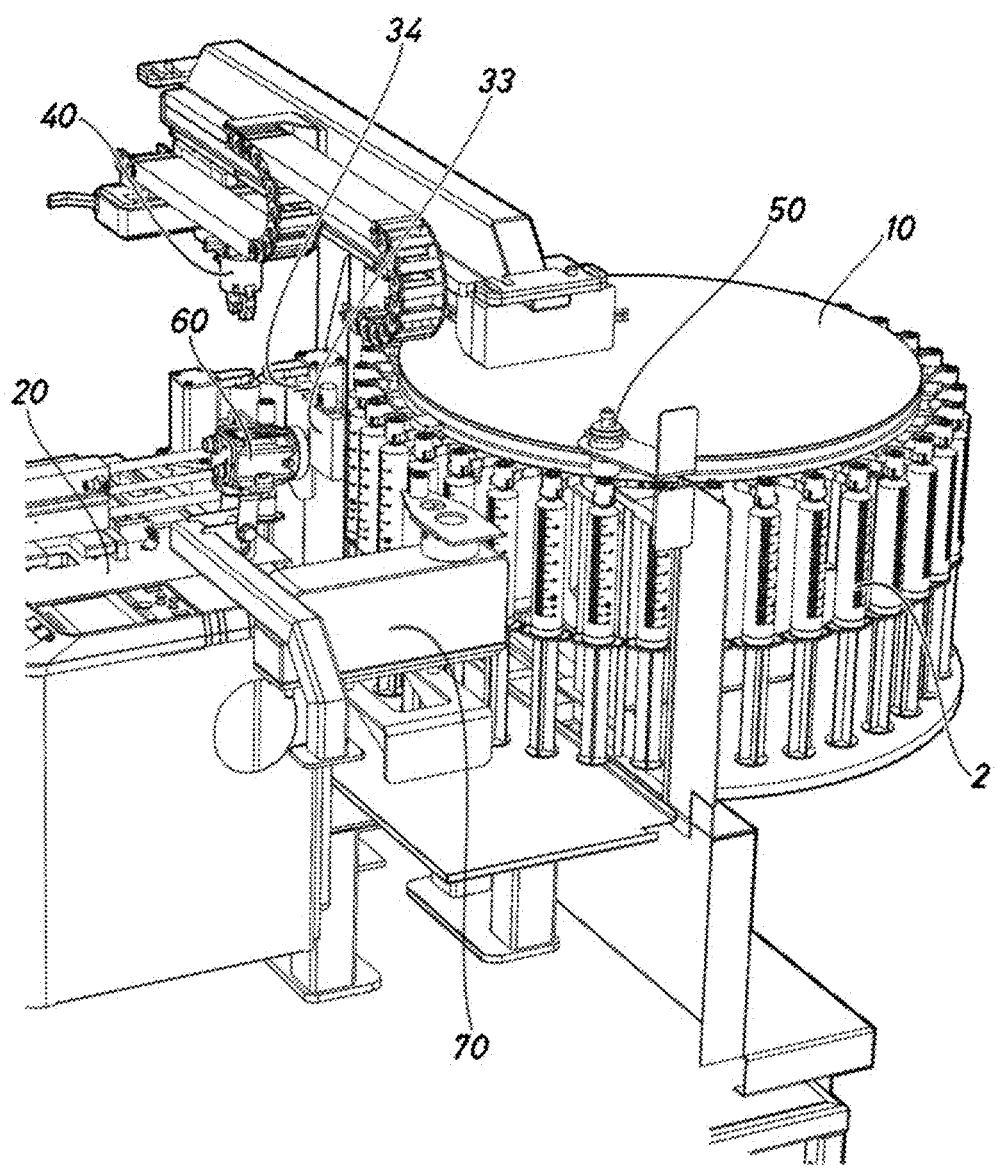
FIG. 10 is a perspective view of the first embodiment of a syringe labelling device according to the present invention without the outer panels and with the support structure removed.

FIG. 10 shows the same elements as FIG. 9 but from another perspective, allowing details to be seen which are concealed in FIG. 9. This figure clearly shows the carousel -10- having a plurality of syringes -2- having disposable RFID labels, and also the RFID label reader -50-, the precision scale -70-, the video camera -60-, the robotic arm -40- and the labelling station.

Next, the operation of the first embodiment of a syringe labelling device according to the present invention will be explained in detail.

The user, in this case a pharmacist or similar, takes the syringes which contain the medicine prepared at the medicine preparation station. In this first embodiment, the syringes -2- have a disposable RFID label. During the preparation of the medicine, the data relating to the medicine contained in the syringe are recorded on the RFID label thereof, such as for example, composition, patient for whom said medicine is intended, etc. Once the medicine has been correctly packaged in the syringe and the RFID label has been written with the corresponding information, the user takes the syringe and places said syringe in the carousel -10- having means for holding and transporting syringes. In the embodiment shown, the carousel -10- can house a maximum of 36 syringes, but other embodiments with a larger or smaller capacity for housing syringes are also possible. The user may then continue loading syringes while the labelling station -1- is operating, so that while the user is positioning syringes in the carousel, the labeller -1- does not need to stop.

Because of the stepper motor which actuates the carousel -10-, said carousel continues rotating whilst the labeller -1- is labelling syringes. The syringe -2- moves forward on the carousel until said syringe is positioned beneath, or approximately beneath, the RFID reader -50-. Said RFID reader -50- reads the corresponding disposable RFID label of the syringe -2-, and allows the contents thereof and the rest of the data to be printed on the label that will be affixed to the syringe -2- to be identified. When the reading of the RFID label of the syringe -2- is complete, the control device of the labeller has identified the syringe -2- and the contents thereof, but the syringe -2- continues to move forward in the carousel -10- until it is the turn of said syringe to be labelled. When a syringe -2- is to be labelled, the robotic arm -40- holds said syringe by the stopper and, in the embodiment shown, takes said syringe to the precision scale -70- to carry out the weighing of said syringe -2-.

Weighing the syringe allows errors to be detected in the dosage or in the writing of the RFID label of the syringe -2-. Once weighing on the precision scale -70- is complete, the data obtained are stored in a database which stores all the data relating to the preparations of medicines. Although weighing the syringe has important advantages for ensuring that the contents of the syringe are correct, embodiments are also possible that do not have a weighing station and that rely only on the data obtained from reading the RFID label.

Once the syringe has been weighed, the robotic arm -40- again takes hold of the syringe -2-, positions said syringe in front of the video camera -60- and rotates said syringe until said video camera -60- detects a previously memorised pattern. Once the pattern has been detected, the control device calculates the necessary rotation to orient the syringe -2- in such a way as to prevent the marker scale thereof from being covered by the label which will later be affixed thereto. As can be seen in the figures, the video camera -60- is positioned on a support which can be adjusted in terms of rotation and height. Said video camera -60- is controlled by specialised software which, by means of the control device, acts in a coordinated manner with the robotic arm -40-.

When the syringe -2- is in a position where the marker scale thereof cannot be covered by the label, the robotic arm transports the syringe -2- to the labelling station -30-. In the labelling station -30-, the printer -20- prints a label with the data obtained from the database and corroborated by the weighing of the syringe carried out earlier (in embodiments that do not have a weighing station, the data for printing on the label are obtained only from the database).

In the embodiment shown, the printer -20- prints labels with a paper support, however, said printer -20- comprises a paper support re-winder responsible for separating the label from the corresponding paper support, so that when the label leaves the label dispenser -23- (see FIGS. 11, 12 and 19) and is taken up by the applicator element -22-, said label is ready to be affixed to the syringe -2-. Before affixing the label to the syringe -2-, the printer -20- checks that the label has been printed correctly by means of sensors, which in the embodiment shown are a bar code reader and a Data Matrix reader.

Once the label is held on the applicator element -22- by suction, and if the sensors detect that the label has been printed correctly, the retractable arm -21- is extended until it reaches the label affixing position. In said affixing position, the applicator element -22- and the label held thereon make contact with the syringe -2- in such a way that the label is affixed tangentially to said syringe -2-. Once the label is tangentially affixed to the syringe -2-, the applicator element ceases suction of the label and the retractable arm -21- returns to the label pick-up position where it waits until the next syringe in the batch is ready to be labelled. If the sensors detect that the label has not been printed correctly, the robotic arm -40- leaves the syringe -2- in the syringe support -34- and holds the substitute support -33-. When the robotic arm -40- is holding the substitute support -33-, the robotic arm -21- passes to the label affixing position and affixes the defective label to the substitute support -33-. Next, the robotic arm -40- positions the substitute support -33- in its support and takes hold again of the syringe -2- which was waiting in the support -34-, and the label printing and affixing process is repeated until said label is printed correctly.

Once the label is affixed tangentially to the syringe -2-, said label must finish by being affixed around the body of the syringe -2-. Accordingly, in this embodiment, the robotic arm -40- holding the syringe -2- by the corresponding stopper causes said syringe to pass through the rollers -31-, -32- in such a way that said rollers apply a uniform force over the body of the syringe so that the label is uniformly affixed over said body. Because of the springs with which the supports -310-, -320- of the rollers -31-, -32- are equipped, variability in the size of the syringes can be accommodated and, consequently, syringes of different sizes and capacities can be labelled. It is important to emphasise that the assembly formed by the supports -310-, -320- and the corresponding rollers -31-, -32- are arranged in such a way that when the syringe -2- passes between the rollers -31-, -32-, as well as applying uniform pressure to the syringe -2-, said rollers put up very little resistance to the passage of said syringe -2-. This is important, because if said rollers were to put up a great deal of resistance to the passage, the stopper of the syringe -2- could be broken, with the resulting spillage of the contents of said syringe and the risk of contamination, etc. this would entail.

The above explanation has been given assuming that the results of the weighing of the syringe coincide with those expected and the preparation, that is, the medicine contained in the syringe, can be regarded as valid. If the weighing of the syringe results in the detection of a possible anomaly, the labelling process would be the same, except that the syringe would be labelled with a label specifying that said syringe is not suitable for administration to a patient. If the reading of the RFID label of the syringe is defective, the syringe would also be labelled as not suitable for administration to the patient.

In the final phase of the labelling process, the robotic arm -40- allows the syringe -2-, already labelled as a preparation that is or is not suitable for use in patients, as the case may be, to fall into a chute -100- (see FIGS. 11, 12 and 17) which takes the syringe -2- to a receptacle for collecting syringes that are suitable for therapeutic use -160- or to a receptacle for syringes that are not suitable for therapeutic use -161- (see FIG. 25). Syringes that are suitable for therapeutic use may be administered to the patient by the appropriate health professionals and syringes that are not suitable must be reviewed by qualified staff and/or suitably destroyed.

In the embodiment shown, the labelling station -30- is capable of labelling using, at least, flag, half-flag and wraparound labels.

Figure 11:
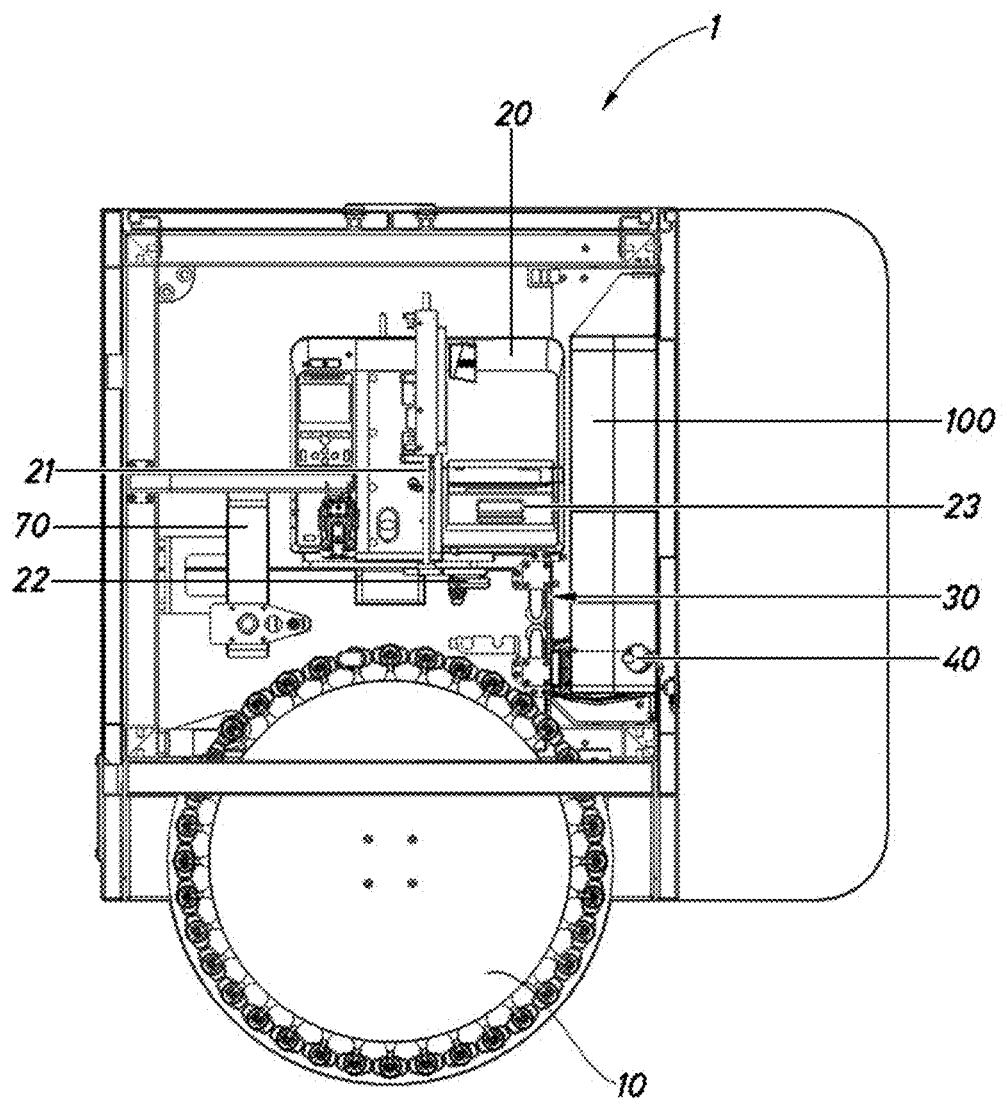
FIG. 11 is a plan view of a cross section of the first embodiment of a syringe labelling device according to the present invention.
Figure 12:
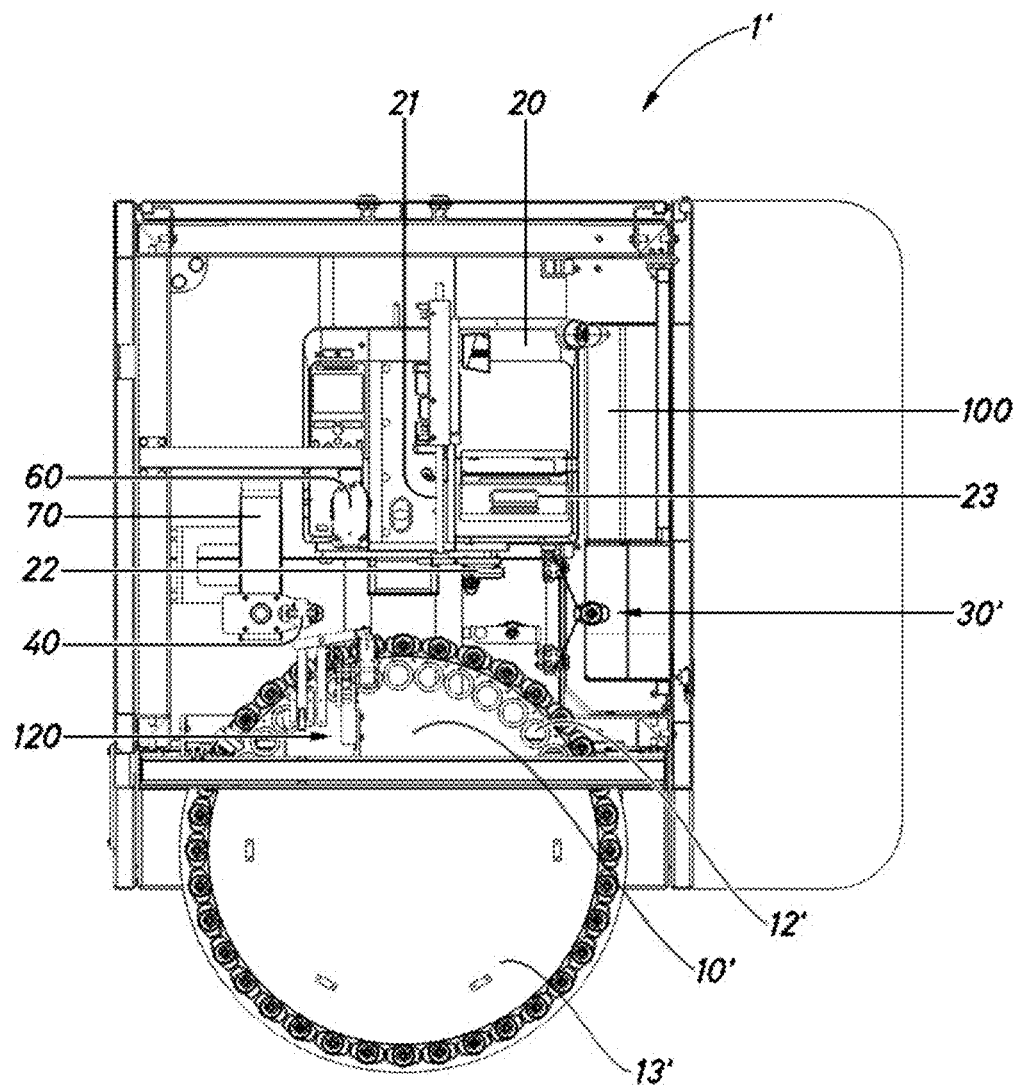
FIG. 12 is a plan view of a cross section of the second embodiment of a syringe labelling device according to the present invention.

FIGS. 11 and 12 show the horizontal distribution of the main components comprised in the two embodiments shown in the present document. As can be seen, both embodiments share a large number of elements. As mentioned earlier, the main difference between the two embodiments is that the first embodiment is intended for labelling syringes with disposable RFID labels and the second embodiment is intended for labelling syringes with reusable RFID labels. This means that the labeller -1'- of the second embodiment has a reusable RFID label removal mechanism -120-.

Another notable difference between the two embodiments shown in FIGS. 11 and 12 resides in the labelling stations -30-, -30'-. As can be seen, the labelling station -30- of the first embodiment comprises two parallel rollers each housed in its own support, whereas the labelling station -30'- of the second embodiment comprises two articulated gates. The typology of the labelling station is independent of the type of syringe to be labelled (with a reusable or disposable RFID label), that is, a syringe labeller using reusable RFID labels may comprise both labelling stations having parallel rollers and labelling stations having articulated gates. The same applies to syringe labellers using disposable RFID labels.

The fact that each of the embodiments shown in FIGS. 11 and 12 label different syringes results in other more minor changes therebetween, such as for example that the labeller -1'- of the second embodiment has no independent RFID reader because said RFID reader is incorporated inside the reusable RFID label removal mechanism -120-. Another element which changes depending on the type of syringe to be labelled is the carousel having means for holding and transporting syringes. As can be seen, the carousel -10'- of the second embodiment comprises on the upper circular plate thereof a plurality of holes -12'-. Each of the holes -12'- of said plurality has dimensions such as to allow the passage therethrough of the reusable RFID label once said RFID label has been removed from the syringe by the removal mechanism -120-. In addition to the above, the carousel -10'- of the second embodiment comprises a protector -13'-which covers and protects the upper circular plate and the plurality of holes -12'-.

Figure 13:
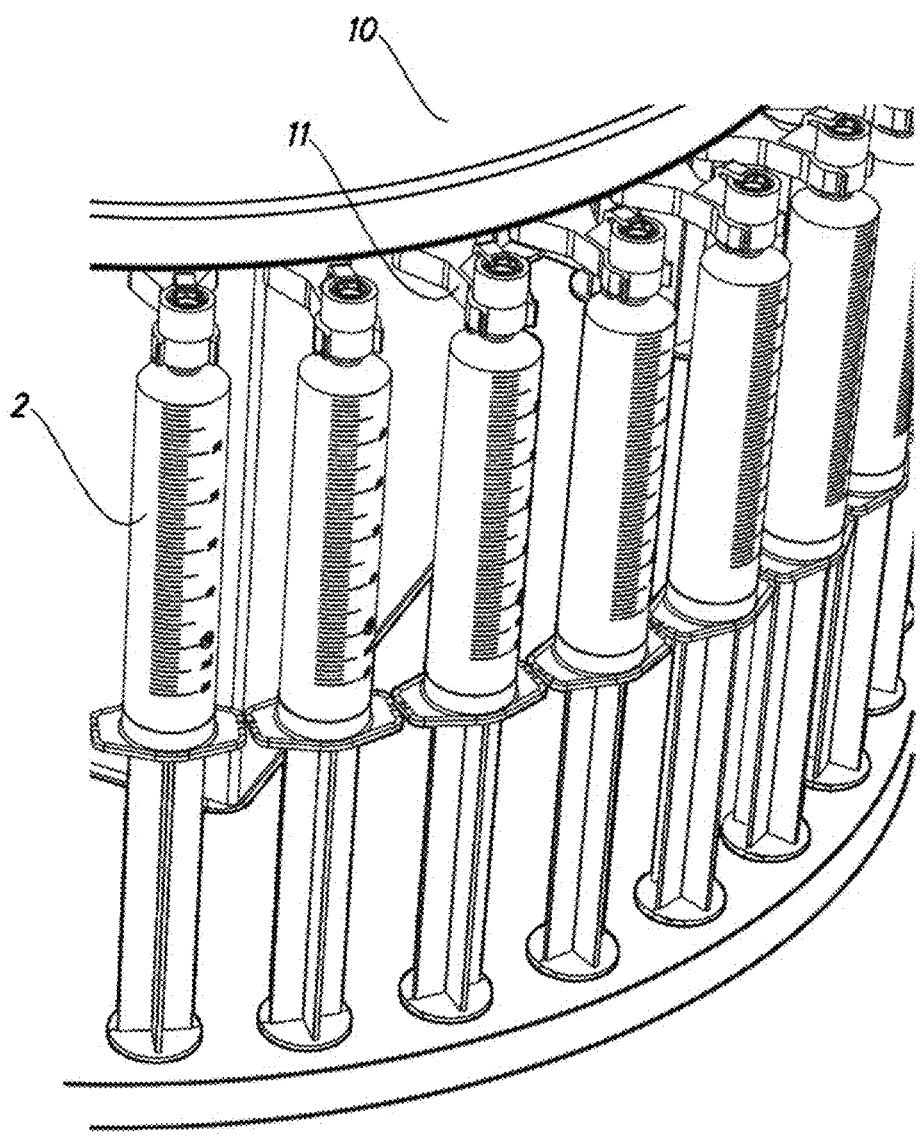
FIG. 13 is a perspective view of a carousel having means for holding and transporting syringes of the first embodiment of a syringe labelling device according to the present invention.
Figure 14:
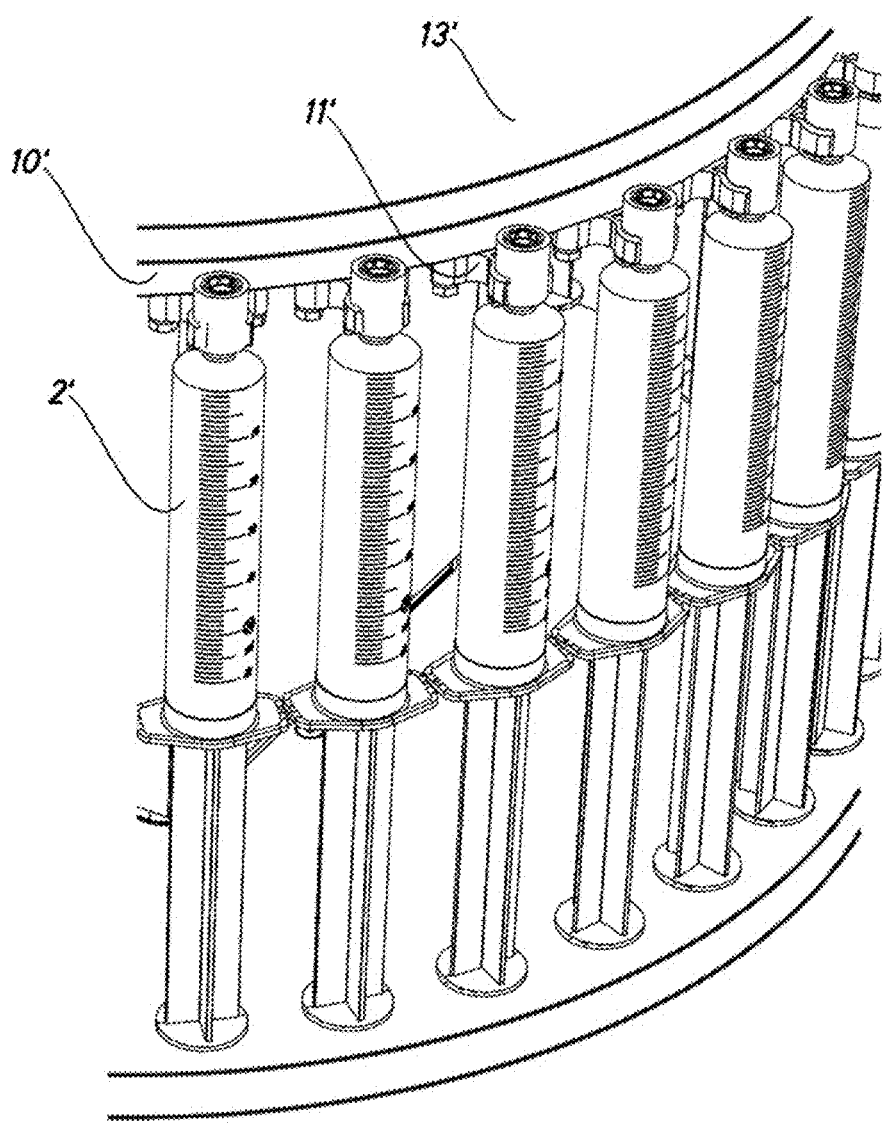
FIG. 14 is a perspective view of a carousel having means for holding and transporting syringes of the second embodiment of a syringe labelling device according to the present invention.

FIGS. 13 and 14 show in perspective a carousel having means for holding and transporting syringes of the first and second embodiments, respectively. As can be seen in both figures, in both embodiments the syringes are held by the stopper by means of a plurality of tabs. Although in both embodiments the syringes are held by the stopper, other embodiments in which the syringes are held by other portions, such as the body, for example, are also possible.

In the first embodiment, the syringe -2- is held by the stopper by means of three deformable tabs -11-, two of which are diametrically opposite and apply a radial force and one holds the stopper from above applying a longitudinal force. As can be seen, the plurality of deformable tabs -11- is attached to the upper circular plate of the carousel -10-. In the second embodiment, two diametrically opposite deformable tabs -11'-, which apply a radial force towards the centre of the stopper, hold the syringe -2'- having a reusable RFID label. In the same way as in the first embodiment, the two deformable tabs -11'- are attached to the upper circular plate of the carousel -10'-. As explained earlier, the upper circular plate of the carousel -10'- is protected by a protector -13'-.

Figure 15:
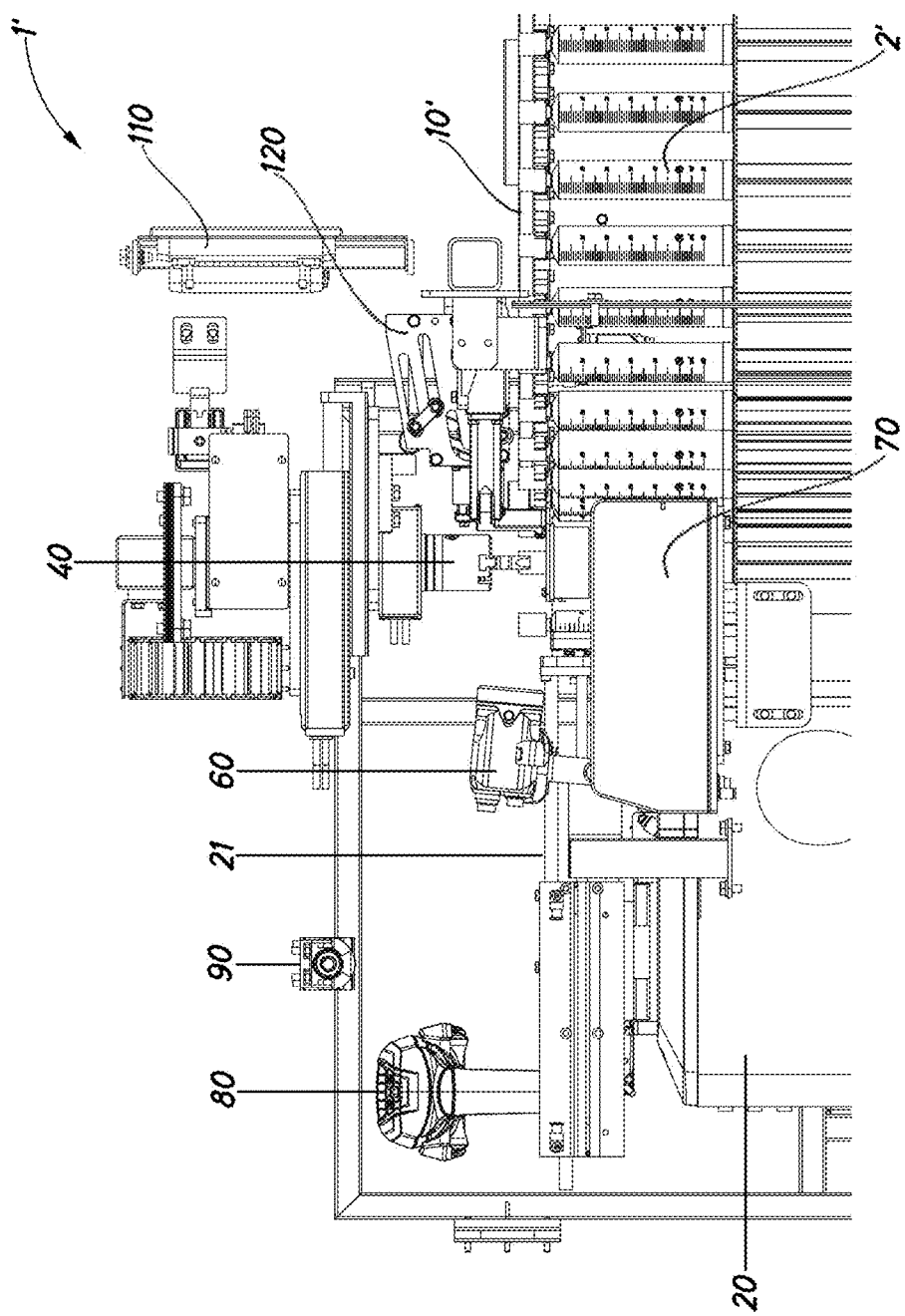
FIG. 15 is a side view of a detail of the second embodiment of the syringe labelling device according to the present invention without the outer panels and with the support structure removed.

FIG. 15 shows a view in profile of a detail of the second embodiment of a syringe labelling device according to the present invention. In a similar way to the other figures, in this figure the outer panels, structures and other elements that may prevent the main components of the labeller -1'- from being seen clearly, have been omitted. In this figure it can clearly be seen that the reusable RFID label removal mechanism -120- is positioned on a higher plane than the carousel -10'- so as to be able to access the reusable RFID label -202- positioned on the stopper -201- of the syringe -2'- (see FIG. 22). As can be seen, and in order to minimise the travel of the robotic arm -40-, the carousel -10'-, the precision scale -70-, the retractable arm -21- of the printer and the relevant applicator element thereof are at approximately the same height. Although not visible in this figure, the labelling station is also at approximately the same height as the above-mentioned elements.

In the embodiment shown in FIG. 15, the video camera -60- is positioned on a slightly higher plane than the retractable arm -21- of the printer -20- and, preferably, is arranged so as to be inclined slightly towards the carousel -10'- in order to have an optimal view of the syringe -2'- and of the marker scale thereof. As can be seen, in the embodiment shown, the robotic arm -40- moves above the carousel -10'-, printer -20-, precision scale -70-, etc., but other embodiments in which the robotic arm -40- moves beneath said elements are also possible.

FIG. 15 also shows the position of the manually operated RFID reader -90- and of the manually operated bar code reader -80-. Although it cannot be seen because in the embodiment in this figure the structural elements and outer panels have been omitted, in this embodiment, the manually operated RFID reader -90- is connected to one of the cross beams of the structure of the labeller -1'- and the manually operated bar code reader -80- is located on a support connected to the structure of the labeller -1'-. The arrangement of both elements is such as to facilitate access thereto by the user when the door -150- (see FIGS. 1 and 25) and/or the rear doors of the labelling device -1'- are opened.

Figure 16:
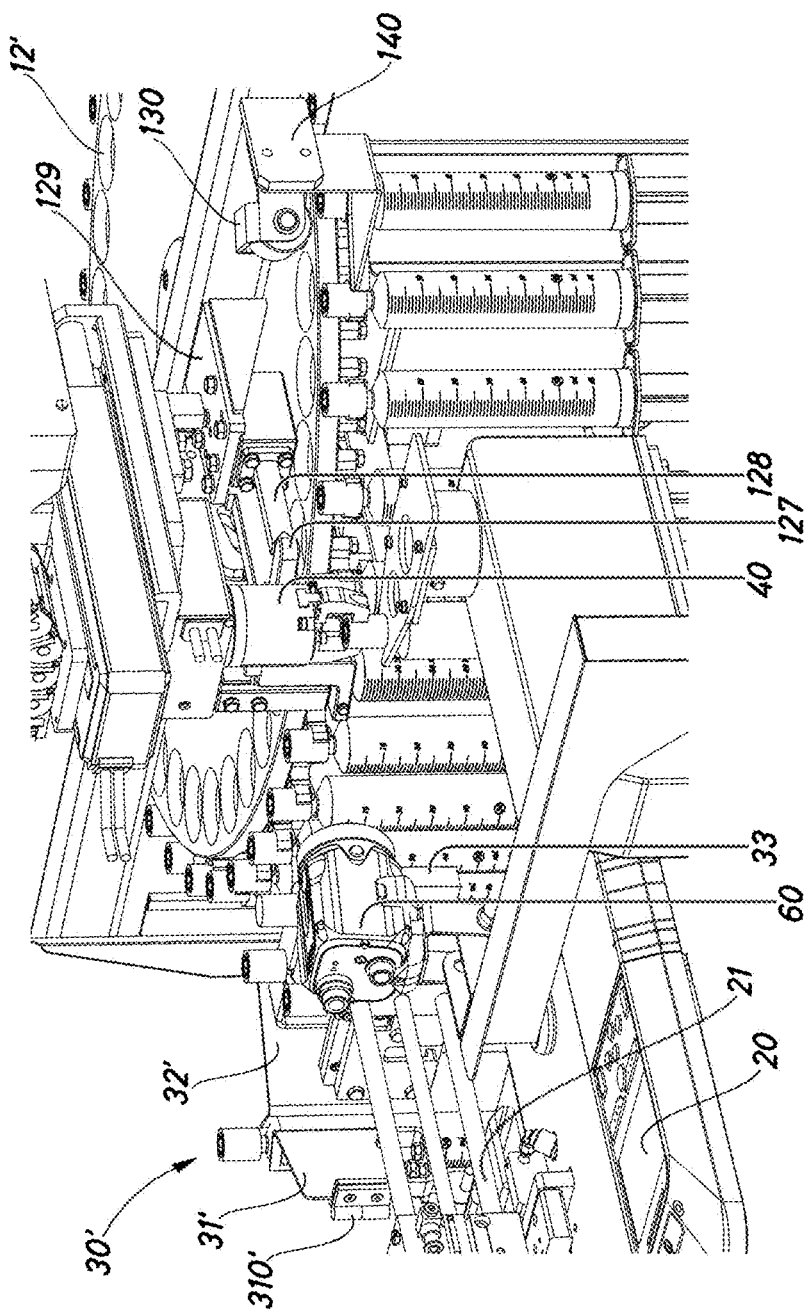
FIG. 16 is a perspective view of the means for detecting the position of the marker scale of the syringes, the syringe handler, the weighing station and other elements of the second embodiment of a syringe labelling device according to the present invention.

FIG. 16 also shows in perspective the labelling station -30'-, the arm -140- and the cam -130- of the second embodiment of a labeller according to the present invention. As can be seen, in the second embodiment the labelling station -30'- comprises a pair of articulated gates -31'-, -32'- arranged in such a way that when the robotic arm -40- causes the syringe -2'- to pass therethrough, said gates apply a uniform pressure over the body of said syringe. The gates -31'-, -32'- are articulated by means of hinges -310'-, -320'- (the hinge -320'- can be seen in FIG. 19) which comprise resilient torsion means. FIG. 16 also shows some of the components of the reusable RFID label removal mechanism -120-, more specifically it shows the support -129- and the rocker arm -127- connected thereto, and the bar -128- which applies a force to said rocker arm -127- so that said rocker arm is capable of holding the syringe. The bar -128- has at one end thereof resilient means housed inside the support -129- which allow said bar to oscillate and apply force to the rocker arm -127-.

Figure 17:
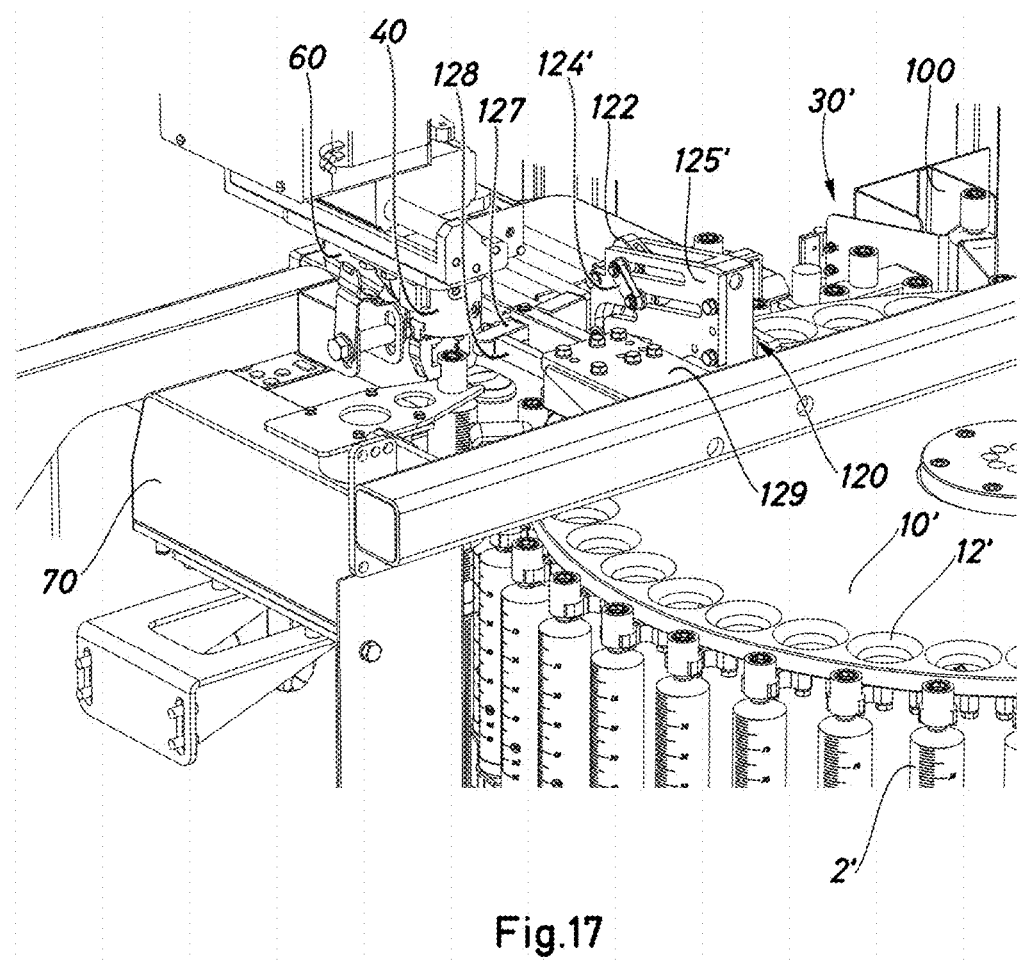
FIG. 17 is a perspective view of the syringe handler, the weighing station, the carousel having means for holding and transporting syringes and the mechanism for removing reusable RFID labels of the second embodiment of a syringe labelling device according to the present invention.

FIG. 17 shows with greater clarity the reusable RFID label removal mechanism -120- because said [figure] shows the main components of the second embodiment of a labeller according to the present invention from another point of view. In this figure, it can be seen that the rocker arm -127- is connected with the possibility of rotation to the support -129- and that said rocker arm -127- is actuated by the bar -128-. This figure also shows the plate -125'- which together with its twin -125- (see FIGS. 18 and 19) acts as a support for the kinematics chain responsible for removing the label holder from the syringe. Moreover, each of the plates -125-, -125'- comprises four grooves along which the nodes of the mechanism slide. As can be seen, one of the links of the removal mechanism -120- comprises a projection -122-, which in the embodiment shown is substantially circular, with which the robotic arm -40- makes contact when going to pick up the next syringe to be labelled in the carousel -10'-.

In addition to the above, FIG. 17 also shows the chute -100- which takes the fully labelled syringes to the receptacle for syringes that are suitable for therapeutic use or to the receptacle for syringes that are not suitable for therapeutic use.

Figure 18:
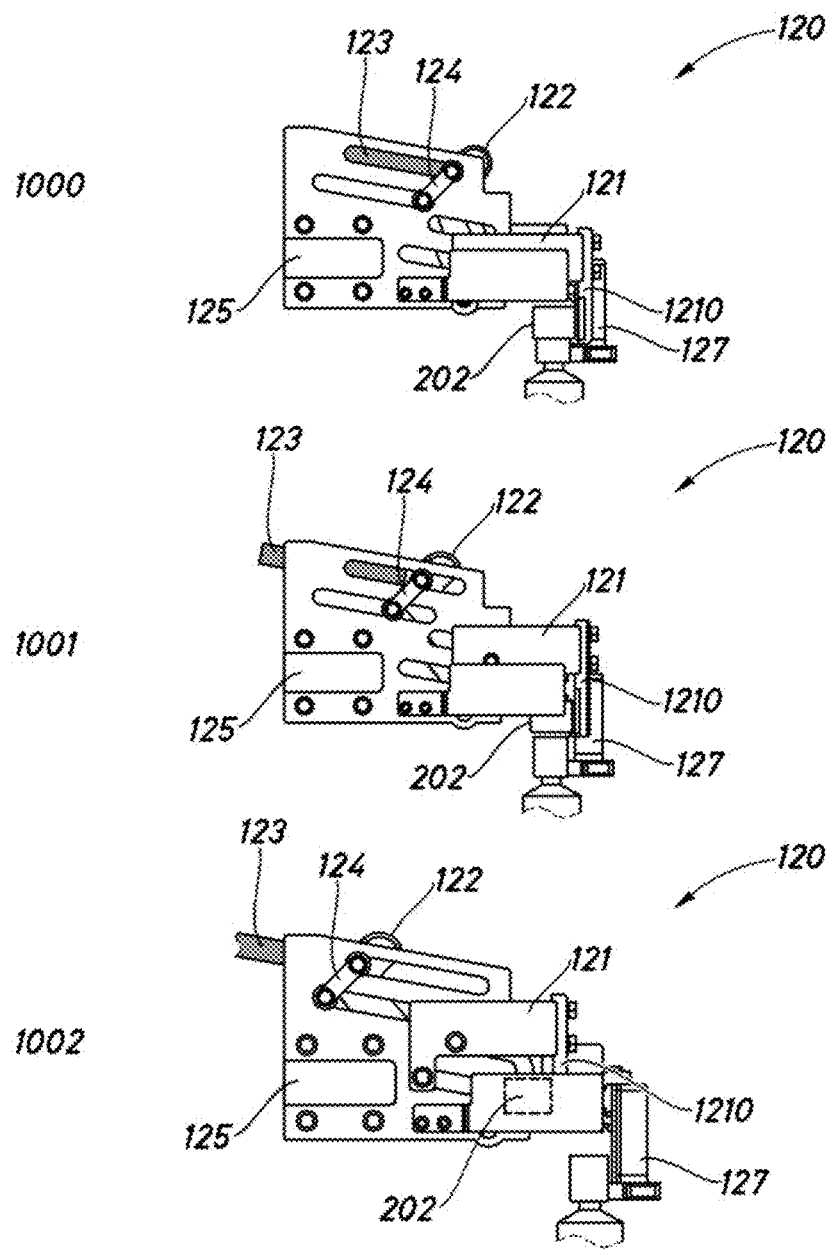
FIG. 18 schematically shows the operation of the reusable RFID label removal mechanism of the second embodiment of a syringe labelling device according to the present invention.

FIG. 18 schematically shows the operation of the reusable RFID label removal mechanism -120-. In the first step -1000-, the rocker arm -127- holds the syringe -2'- by the stopper thereof and does not hold the label holder which comprises the reusable RFID label -202-. Thus, the syringe -2'- is prevented from rising during the process of removing the label holder and the reusable RFID label -202- comprised therein.

In the embodiment shown, the removal mechanism -120- comprises two L-shaped parts -121-, -1210- which are connected together and form a 'hook' responsible for removing the label holder from the syringe -2'-. The part -121- comprises a pair of through-shafts which in turn slide along the respective grooves in the plates -125-, -125'-. As can be seen, the link which comprises the projection -122- is also connected to a telescopic piston -123- and to the binary link -124- and its twin -124'- (not shown). The link which comprises the projection -122- is connected by the other end thereof to one of the shafts comprised in the part -121-. The other shaft comprised in said part -121- is connected by a binary link to the binary link -124-. As can be seen, the connection of the binary link -124- to the remaining elements mentioned is made by means of through-shafts which slide along the two other grooves comprised in the plates -125-, -125'-.

In the second step -1001-, the robotic arm -40- (not shown in this figure) makes contact with the projection -122- so as to actuate the removal mechanism -120-. When sliding along the grooves, the 'hook' applies a force in the axial direction of the syringe so as to be able to remove the label holder and the corresponding reusable RFID label -202- from the stopper of the syringe -2'-.

In the third step -1002-, the connection nodes between the links, which are actuated by the robotic arm -40- (not shown in this figure), slide along the corresponding groove and arrive at the relevant end-of-travel position, at which moment the hook ceases to hold the label holder and the reusable RFID label -202- incorporated therein and falls through the corresponding hole -12'- in the upper circular plate of the carousel -10'- (see, among others, FIGS. 2, 3, 12 and 17).

Once the robotic arm moves away together with the syringe to continue the labelling process, the removal mechanism -120- ceases to be actuated and returns to the rest position so as to wait for the next syringe of the carousel having means for holding and transporting syringes.

During the process of removing the label holder and the relevant reusable RFID label -202- thereof, the RFID reader (not shown) incorporated in the removal mechanism -120- reads said RFID label. The operation of the RFID reader incorporated in the removal mechanism is similar to that of the RFID reader -50- of the first embodiment of a syringe labelling device according to the present invention shown and described earlier.

Figure 19:
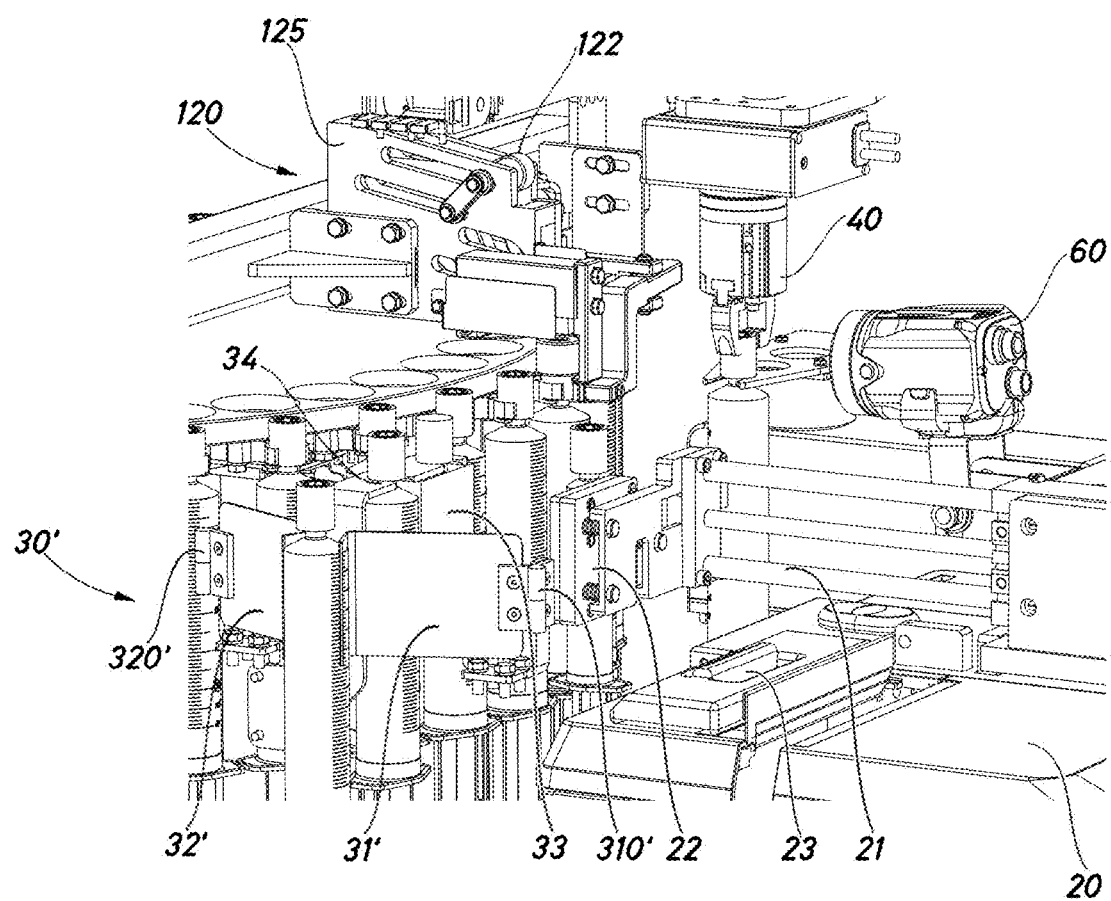
FIG. 19 is a perspective view of the labelling station, of the reusable RFID label removal mechanism, of the syringe handler and of the means for detecting the position of the syringes of the second embodiment of a syringe labelling device according to the present invention.
Figure 20:
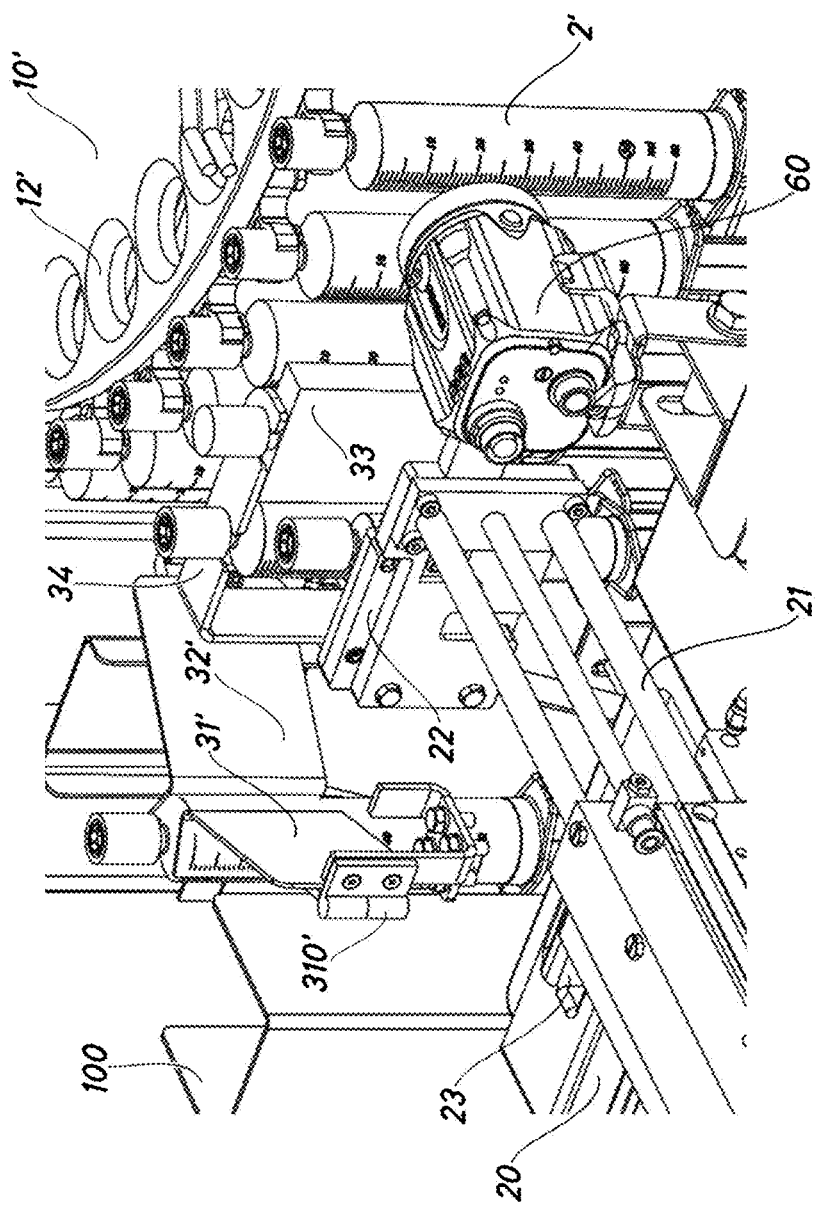
FIG. 20 is a perspective view of the labelling station of the second embodiment of a syringe labelling device according to the present invention.

FIGS. 19 and 20 show clearly the labelling station -30'-, the reusable RFID label removal mechanism -120-, the printer -20- and the rest of the main elements of the second embodiment of a labeller according to the present invention. This figure shows that the labelling station -30'- comprises the articulated gates -31'-, -32'- as well as the respective hinges thereof -310'-, -320'- and the syringe support -34- and the substitute support -33- for affixing badly printed or defective labels. This figure also shows the label printer -20-, as well as the retractable arm -21-, the applicator element -22- and the label dispenser -23-, which is aligned with the applicator element -22-. As can be seen, said applicator element -22- is connected to a plate which is rigidly connected to the retractable arm -21- by a plurality of springs, which allows said applicator to absorb the small impacts which are produced when the label is placed on the syringe.

Figure 21:
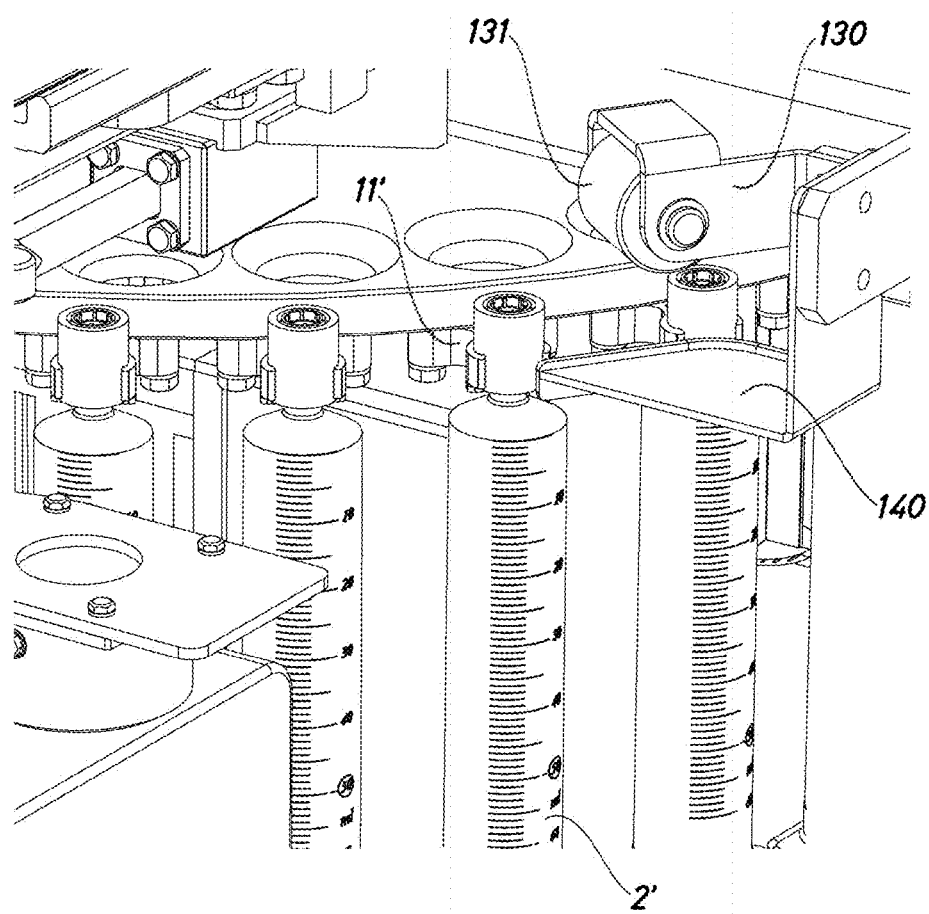
FIG. 21 is a perspective view of the roller and of the arm for repositioning badly positioned syringes on the carousel of the second embodiment of a syringe labelling device according to the present invention.

FIG. 21 is a perspective view of the roller and of the arm for repositioning badly positioned syringes on the carousel of the second embodiment of a syringe labelling device according to the present invention. As can be seen, this embodiment has an L-shaped arm -140- with one of the ends thereof at an angle so as to be able to laterally reposition the badly positioned syringes on the carousel, more specifically, in the two tabs -11'- which, in this embodiment, hold the syringes by the stopper thereof. In addition, this embodiment has a roller -131- of which the shaft is mounted in a cam -130- and which is arranged so as to vertically reposition the badly positioned syringes in the corresponding support -11'-. In the embodiment shown, both the arm -140- and the cam -130- with the roller thereof -131- are positioned close to the point where the syringes enter the syringe labelling device.

Both the arm -140- and the cam -130- with the roller thereof -131- are optional elements which may be included in labellers that label syringes with reusable RFID labels and labellers that label syringes with disposable RFID labels.

Figure 22:
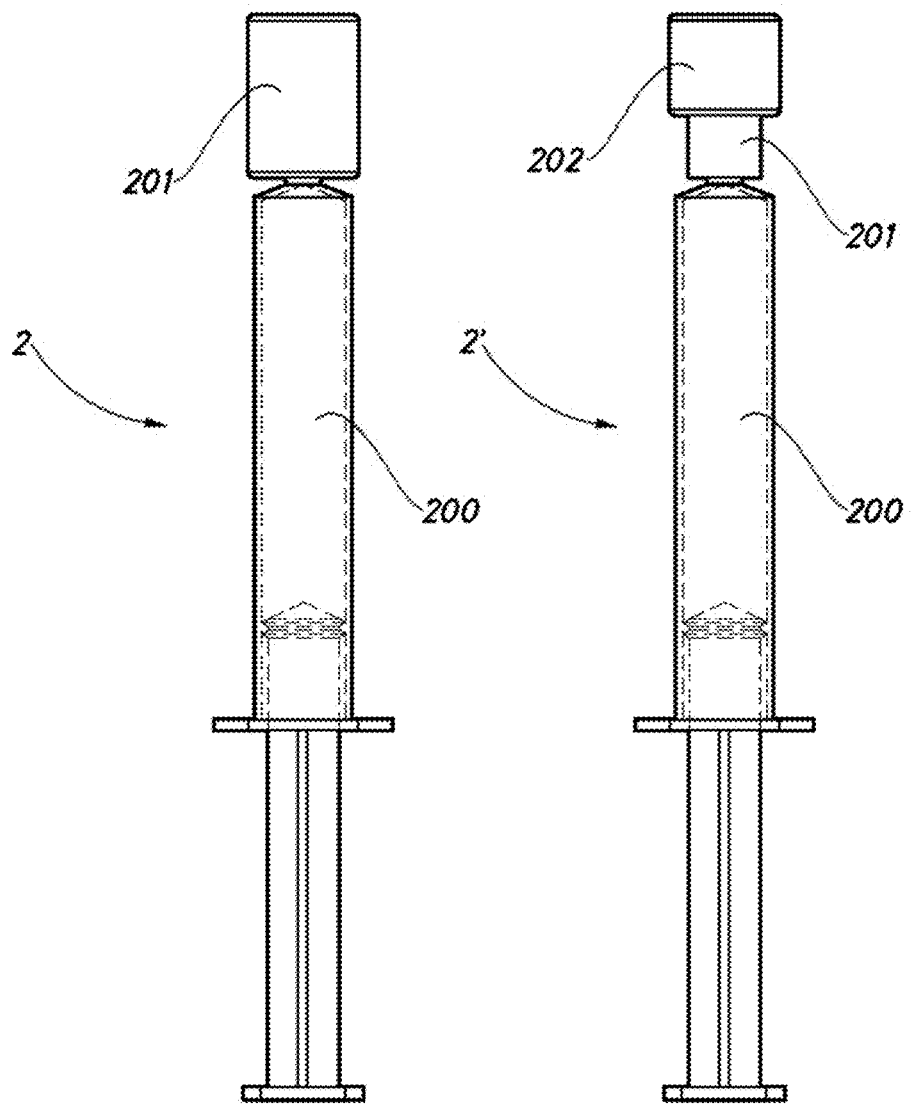
FIG. 22 schematically shows a syringe having a disposable RFID label and a syringe having a reusable RFID label.

FIG. 22 schematically shows a syringe -2- having a disposable RFID label and a syringe -2'- having a reusable RFID label. In both syringes, the body -200- is similar, the differences are in the stopper -201- which hermetically seals the relevant syringe, because in the syringe -2- said stopper incorporates an RFID label whereas the stopper of the syringe -2'- does not have a label. Given that the stopper of this type of syringe is a single-use element, the fact that the syringe -2- incorporates the RFID label in the stopper -201- means that said RFID label is also single use, which increases the cost of said syringe -2-. On the contrary, the stopper -201- of the syringe -2'- only performs the function of stopper and does not have an RFID label, however, given the need to identify each of the syringes with certainty, added to the stopper -201- of the syringe -2'- is a label holder which comprises an RFID label -202-. Said label holder is made of an elastomeric material and is held on the stopper -201- by dimensional interference.

Figure 23:
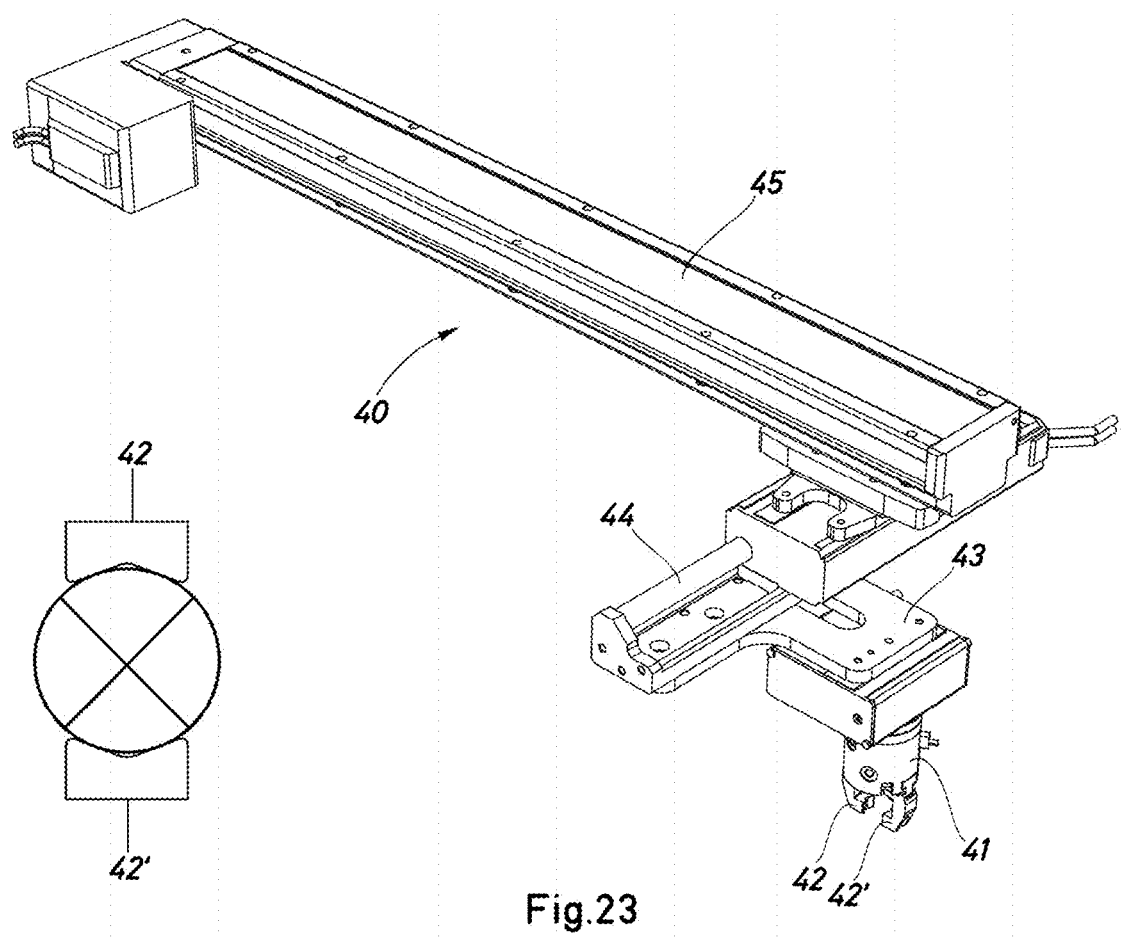
FIG. 23 shows in perspective the syringe handler of the first embodiment of a syringe labelling device according to the present invention.

FIG. 23 shows in detail the robotic arm -40- which preferably, although not only, acts as a syringe handler. The robotic arm shown is capable of moving through the longitudinal guide -45- and the transverse guide -44-, that is, said arm is capable of moving freely through a plane, in this case, a horizontal plane. The embodiment shown does not allow movements in height, although other embodiments in which the robotic arm can also move in height are also possible.

The robotic arm shown comprises a clamp -41- which in turn comprises two symmetrical claws -42-, -42'-which allow the stopper of the syringe to be held by at least three points of contact, although preferably the clamp-stopper hold is produced at four points. In the embodiment shown, the claws -42-, -42'- have pneumatic actuation means, although in other embodiments the claws are actuated electrically. The clamp -41- is capable of rotating freely about its own axis, a characteristic which allows said clamp to be able to rotate the syringe in order to orient said syringe in such a way that the label does not subsequently conceal the marker scale of said syringe. In the embodiment shown, the clamp -41- is connected to a metal sheet -43- and is in turn connected to the transverse guide -44-.

Figure 24:
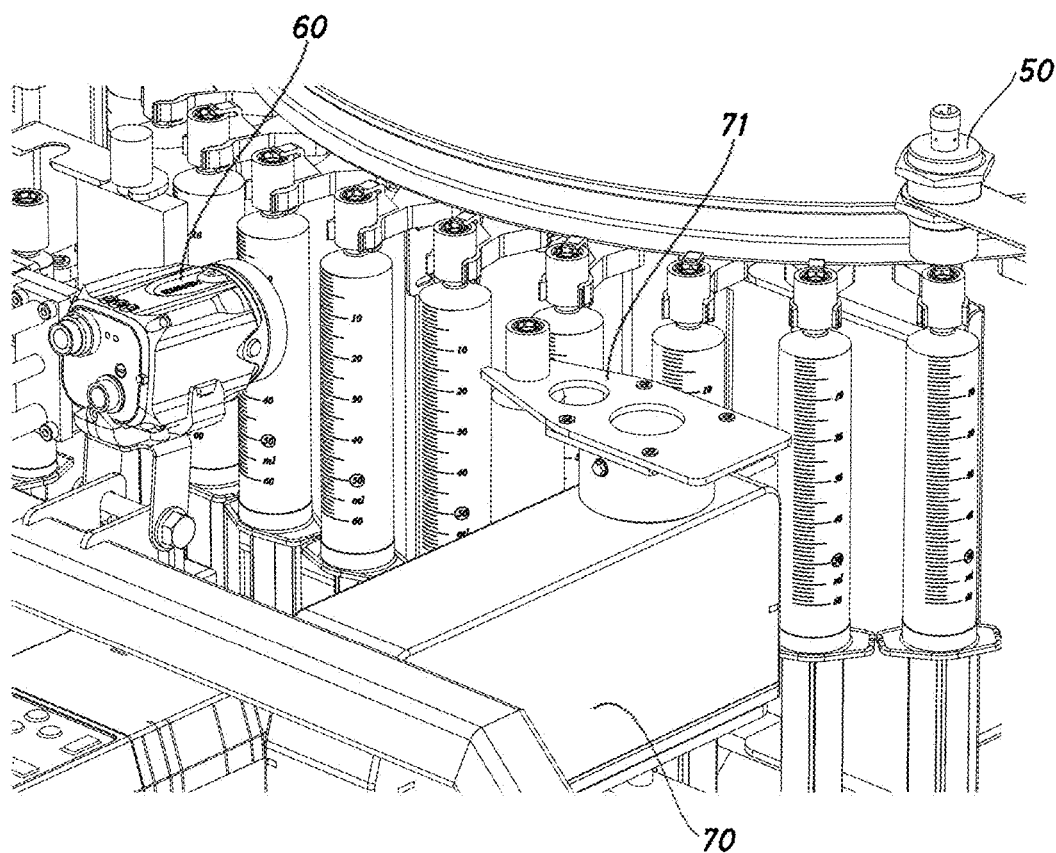
FIG. 24 shows in perspective the weighing station and the RFID label reader of the first embodiment of a syringe labelling device according to the present invention.

FIG. 24 shows in detail the precision scale -70- which acts as a weighing station of the syringe. As mentioned earlier, despite being recommended owing to the numerous advantages provided thereby, the syringe weighing station is not an indispensable component in a syringe labelling device according to the present invention. In the embodiment shown, the precision scale -70- is mounted above at least one silent block so that said silent block can absorb possible vibrations in order to ensure the most precise possible reading by the precision scale -70-. The scale -70- of the embodiment shown in this figure is precise to 10 mg. As can be seen, the precision scale -70- has a support -71- shaped such that the syringes can be held in the space between the stopper of the syringe and the body of said syringe.

FIG. 25 shows the first embodiment of a labeller according to the present invention configured to operate automatically and configured to operate manually. In automatic operating mode -2000-, the mode which achieves maximum productivity from the labeller -1-, all the panels and doors of the labeller are closed, the receptacle for syringes suitable for medical use and the receptacle for syringes that are not suitable for medical use -160-, -161- are positioned above the support -171- and the user can input the necessary commands, etc. via the screen -110-. However, when the labeller -1- operates manually -2001-, the side door -150- is opened so that the user has access to the internal elements of the labeller -1-, more specifically to the printer -20-, to the manually operated bar code reader -80- and to the manually operated RFID reader -90- (see, among others, FIGS. 6 and 8). In manual operation, the user (normally a pharmacist or similar) takes the syringe in his or her hand and reads the RFID label thereof by means of the manually operated RFID reader. Once the RFID label has been read, the printer prints the label which is to be placed on that syringe and the user manually affixes said label thereto and finally places said syringe in the appropriate receptacle -160-, -161-.

The two embodiments shown in the present document allow both manual operation and automatic operation. However, other embodiments in which the labeller can only operate in automatic mode or in manual mode are also possible.

In the figures which show an embodiment of the labelling device which labels syringes with reusable RFID labels, the label holder of the syringes has not been shown in order to make it easier to see how said syringes are held. Said label holder and the positioning thereof on the syringes can be seen clearly in FIG. 22.

It should be noted that, purely for illustrative purposes, the carousel has been shown in the figures having a syringe in each of the plurality of holding tabs. In normal operation of the labelling device, the carousel having means for holding and transporting syringes will empty as the syringes held therein are labelled.

Although the invention has been set out and described with reference to embodiments thereof, it should be understood that these do not limit the invention, and that it is possible to alter many structural or other details that may prove obvious to persons skilled in the art after interpreting the subject matter disclosed in the present description, claims and drawings. In particular, in principle and unless otherwise explicitly stated, all the features of each of the different embodiments and alternatives shown and/or suggested may be combined with each other. Therefore, the scope of the present invention includes any variant or equivalent that could be considered covered by the broadest scope of the following claims.

What is claimed is:

1. A labelling device for syringes for pharmaceutical products which comprises:
a carousel including a syringe holder and a syringe transporter;
a syringe labelling station;
a syringe handler; and
a camera configured to detect a position of a marker scale of each syringe,
wherein the syringe handler is a robotic arm configured to rotate each syringe in order to orient said syringe in such a way that a label does not conceal the marker scale of said syringe, and
wherein the syringe labelling station comprises an arm responsible for holding the label by a suction system and two articulated gates arranged such that when the syringe handler causes each syringe to pass therethrough, said gates apply pressure over the body of each syringe in such a way that the label is affixed uniformly over said body.

2. The device according to claim 1, wherein each of the articulated gates comprises at least one hinge.

3. The device according to claim 1, further comprising at least one RFID reader, a control device and a label printer wherein the control device is configured to transmit data read by the at least one RFID reader to the label printer.

4. The device according to claim 1, wherein the labelling station also comprises a sensor for detecting correct printing of the labels of the syringes.

5. The device according to claim 4, wherein the labelling station also comprises a support for badly labelled syringes and a substitute support where defective labels are affixed.

6. The device according to claim 1, further comprising a reusable RFID label removal mechanism which in turn comprises a reusable RFID label reader, wherein said reusable RFID label removal mechanism is actuated by the syringe handler.

7. The device according to claim 6, wherein the reusable RFID label removal mechanism also comprises a mechanism having three binary links, each of nodes of said binary links being housed in a corresponding groove along which said nodes slide when said mechanism is actuated, one of said binary links being actuated by the syringe handler.

8. The device according to either claim 6, wherein reusable RFID label removal mechanism comprises means for holding the stopper of the syringe during the removal of the reusable RFID label.

9. The device according to claim 6, wherein the an upper circular plate of the carousel comprises a hole for each of the syringes which said carousel can hold, said hole being suitable for the passage therethrough of the reusable RFID label of the corresponding syringe.

10. The device according to claim 1, further comprising a precision scale, wherein a control device compares the reading of said precision scale with the reading of the at least one RFID reader.

11. The device according to claim 1, wherein the camera configured to detect the position of the marker scale of the syringes comprises a video camera.

12. The device according to claim 1, wherein the syringe handler comprises a clamp which holds the syringe by at least three points.

13. The device according to claim 1, further comprising at least one receptacle for syringes that are suitable for therapeutic use and at least one receptacle for syringes that are not suitable for therapeutic use.

14. The device according to claim 1, further comprising a roller of which a shaft is mounted in a cam and which is arranged so as to vertically reposition syringes that are badly positioned on the carousel.

15. The device according to claim 1, further comprising an arm which laterally repositions syringes that are badly positioned on the carousel.

16. The device according to claim 1, further comprising a bar code reader.

* * * * *

UNITED STATES PATENT AND TRADEMARK OFFICE
CERTIFICATE OF CORRECTION

PATENT NO. : 10,654,608 B2
APPLICATION NO. : 16/105250
DATED : May 19, 2020
INVENTOR(S) : Borja Lizari Illarramendi Page 1 of 1

It is certified that error appears in the above-identified patent and that said Letters Patent is hereby corrected as shown below:

- In Column 19, Line 7, Claim 8, delete "either claim" and insert -- claim --.

- In Column 19, Line 9, Claim 8, delete "during the removal" and insert -- during removal --.

- In Column 19, Line 11, Claim 9, delete "wherein the an upper circular plate" and insert -- wherein an upper circular plate --.

Signed and Sealed this
Twenty-fifth Day of August, 2020

Andrei Iancu
*Director of the United States Patent and Trademark Office*